United States Patent [19]
Schellenberg et al.

[11] Patent Number: 5,449,604
[45] Date of Patent: Sep. 12, 1995

[54] CHROMOSOME 14 AND FAMILIAL ALZHEIMERS DISEASE GENETIC MARKERS AND ASSAYS

[75] Inventors: Gerard D. Schellenberg; Thomas D. Bird; Ellen M. Wijsman, all of Seattle, Wash.

[73] Assignee: University of Washington, Seattle, Wash.

[21] Appl. No.: 964,151

[22] Filed: Oct. 21, 1992

[51] Int. Cl.$^6$ .................... C12Q 1/68; C12P 19/34
[52] U.S. Cl. ........................ 435/6; 435/91.2
[58] Field of Search .............. 435/6, 91.2; 536/24.31, 536/23.1

[56] References Cited
PUBLICATIONS

Nechiporuk et al., Am. J. Med. Genet. 48:63-66 (1993).
St. George-Hyslop et al. Genetics 2: 330-334 (1992).
Marx, Science 258: 550 (1992).
Bonnycastle et al., Neurosc. Lett. 160: 33-36 (1993).
Tanzi et al., Society of Neuroscience Abstracts 19: 1255 (1993).
Lannefeit et al. Genetics 2: 330-334 (1992).
Schellenberg et al., American J. Human Genetics, 53: 619-628 (1993).
van Broeckhoven et al. Genetics 2: 335-339 (1992).
St. George-Hyslop, P. H., Tanzi, R. E., Polinsky, R. J., Haines, J. L., Nee, L., Watkins, P. C., Myers, R. H., Feldman, R. G., Pollen, D., Drachman, D., Growdon, J., Bruni, A., Foncin, J-F., Salmon, D., Frommelt, P., Amaducci, L., Sorbi, S., Piacentini, S., Stewart, G. D., Hobbs, W., Conneally, P. M., and Gusella, J. F. The genetic defect causing familial Alzheimer's disease maps on chromosome 21. Science 235:885-890 (1987a).
Bird, T. D., Lampe, T. H., Nemens, E. J., Miner, G. W., Sumi, S. M., Schellenberg, G. D. Familial Alzheimer's disease in American descendants of the Volga Germans: Probable genetic founder effect. Ann. Neurol. 23, 25-31 (1987).
Bird, T. D., Sumi, E. J., Nemens, E. J., Nochlin, D., Schellenberg, G. D., Lampe, T. H., Sadovnick, A., Chui, H., Miner, G. W., Tinklenberg, J. Phenotypic heterogeneity in familial Alzheimer's disease: A study of 24 kindreds. Ann Neurol 25: 12-25 (1989).
Heston, L. L., et al, Linkage of an Alzheimer disease
(List continued on next page.)

*Primary Examiner*—Margaret Parr
*Assistant Examiner*—Lisa B. Arthur
*Attorney, Agent, or Firm*—Christensen O'Connor Johnson & Kindness

[57] ABSTRACT

Method for isolating a DNA segment indicative of an Alzheimer's disease trait in a family population, wherein said family population consists essentially of a plurality of blood relatives of an individual having a chromosome 14 Alzheimer's disease trait, by: preparing a test sample of immobilized separated genomic DNA fragments from a plurality of the blood relatives, contacting each of the test samples with a test oligonucleotide under conditions permitting hybridization of complementary single stranded DNA molecules, wherein the test oligonucleotide is complementary with at least a portion of a genetic marker located between band q11.2 and band q32.1 in chromosome 14, identifying a plurality of hybridized molecules so formed as alleles of the genetic marker in the family population, identifying one of the genetic marker alleles as indicative of the Alzheimer's disease trait in the family population by either determining by pedigree analysis a segregation value for each of the genetic markers alleles and the Alzheimer's disease trait, and selecting an indicative genetic marker allele that co-segregates with the Alzheimer's disease trait in the family population, or measuring genetic linkage between each of the genetic marker alleles and the Alzheimer's disease trait, and selecting a genetic marker allele as indicative of the Alzheimer's disease trait in the family population if the selected genetic marker allele has a maximal LOD score of at least 3 at a recombination fraction of about 0.0 to about 0.1 for genetic linkage with the Alzheimer's disease trait in the family population, and isolating a chromosome 14 DNA segment containing the indicative genetic marker allele.

5 Claims, 6 Drawing Sheets

CHROMOSOME 14

OTHER PUBLICATIONS susceptibility locus to markers on human chromosome 21. Am J Med Genet 40: 449–453 (1991).

Schellenberg, G. D., Pericak-Vance, M. A., Wijsman, E. M., Moore, D. K., Gaskell, P. C., Yamaoka, L. A., Bebout, J. L., Anderson, L., Welsh, K. A., Clarke, C. M., Martin, G. M., Roses, A. D., and Bird, T. D. Linkage analysis of familial Alzheimers's disease using chromosome 21 markers. Am J Hum Genet 48: 563–583 (1991).

Goate, A. M., et al., Segregation of a missense mutation in the amyloid precursor protein gene with familial Alzheimers's disease. Nature 349: 704–706 (1991).

Chartier-Harlin, M.-C., Crawford, F., Houlden, H., Warren, A., Hughes, D., Fidani, L., Goate, A., Rossor, M., Roques, P., Hardy, J., and Mullan, M. Early-onset Alzheimer's disease caused by mutation at codon 717 of the β-amyloid precursor protein gene. Nature 353: 844–846 (1991).

Levy, E, et al., Mutation of the Alzheimers disease amyloid gene in hereditary cerebral hemorrhage, Dutch type. Science 248: 1124–1126 (1990).

Murrell, J., Farlow, M., Ghetti, B., Benson, M. D. A mutation in the Amyloid Precursor protein associated with hereditary Alzheimer's disease. Science 254: 97–99 (1991).

Schellenberg, G. D., et al., Association of an Apolipoprotein CII allele with familial dementia of the Alzheimer type. J Neurogenet 4: 97–108, (1987).

Pericak-Vance, M. A., Bebout, J. L., Gaskell, P. C., Yamoka, L. A., Hung, W-Y., Heyman, A., Clark, C. M., and Roses, A. D. Linkage studies in familial Alzheimer's disease: evidence for chromosome 19 linkage. Am J Hum Genet 48: 1034–1050 (1991).

Naruse, S., et al., Mis-sense mutation Val–Ile in exon 17 of amyloid precursor protein gene in Japanese familial Alzeheimer's disease. Lancet 337: 978–979 (1991).

Yoshida, K., Miki, T., Katsuya, T., Ogihara, T., and Sakaki, Y. The $^{717}$Val-Ile substitution in amyloid precursor protein is associated with familial Alzheimer's disease regardless of ethnic groups. Biochem Biphys Res Comm 178: 1141–1146 (1991).

Schellenberg, G. D., et al., APP$_{717}$, APP$_{693}$, and PRIP gene mutations are rare in Alzheimer disease. Am J Hum Genet 49: 511–517 (1991).

Van Duinj, C. M., et al., Amyloid precursor protein gene mutation in early-onset Alzheimer's disease. Lancet 337: 978 (1991).

Chartier-Harlin, M.-C., Crawford, F., Hamandi, K., Mullan, M., Goate, A., Hardy, J. Backhovens, H., Martin, J-J., Van Broeckhoven, C. Screening for the β-amyloid precusor mutaiton (APP717:Val→Ile) in extended pedigrees with early-onset Alzheimer's disease. Neurosci. lett. 129, 134 (1991).

Crawford, F., et al., Neurosci. Lett. 133, 1 (1991).

Pericak-Vance, M. A., et al., Exp. Neurol. 102, 271 (1988).

Van Duijn, C. M., et al., Familial aggregation of Alzheimer's disease and related disorders—A collaborative re-analysis of case-control studies. Int J Epidemiol 20: S13–S20, 1991.

Mohs, R. C., et al., Arch. Gen. Psychiatry 44, 405 (1987).

Heston, L., et al. Dementia of the Alzheimer type. Arch. Gen. Psychiatry 38: 1085–1090, 1981.

Rapoport, S. I., et al., Neurology 41, 1549 (1991).

Nee, L. E., et al., Neurology 37, 359 (1987).

Breitner, J. C. S., et al., Neurobiol. Aging 13, S66.

Bergem, A. L. M., Engedal, K., Kringlen, E. Twin concordance and discordance for vascular dementia and dementia of the Alzheimer type. Neurobiol. Aging 13, S66, (1992).

Schellenberg, G. D., Bird, T. D., Wijsman, E. M., Moore, D. K., Boehnke, M., Bryant, E. M., Lampe, T. H., Sumi, S. M., Deeb, S. M., Beyreuther, K., and Martin, G. M. Absence of linkage of chromosome 21 q21 markers to familial Alzheimer's disease in autopsy-documented pedigrees. Science 241: 1507–1510 (1988).

St George-Hyslop, P. H., Haines, J. L., Farrer, L. A., Polinsky, R., Van Broeckhoven, C., Groate, A., Crapper McLachlan, D. R., Orr, H., Bruni, A. C., Sorbi, S., Rainero, I., Foncin, J-F., Pollen, D., Cantu, J-M., Tupler, R., Voskresenskaya Mayeux, R., Growdon, J., Myers, R. H., Nee, L., Backhovens, H., Martin, J-J., Rossor, M., Owen, M. J., Mullan, M., Percy, M. E., Karlinsky, H., Rich, S., Heston, L., Montesi, M., Mortilla, M., Macmias, N., Gussella, J. F., and Hardy, J. A. Genetic linkage studies suggest that Alzheimer's disease is not a single homogeneous disorder. Nature 347:194–197 (1990).

Tanzi, R. E., et al., Molecular Genetics of Alzheimer disease amyloid. J Biol Chem 266: 20579–20582, 1990.

Schellenberg, G. D., et al., Ann. Neurol. 31, 223 (1992).

Tanzi, R. E., St Geroge-Hyslop, P. H., Haines, J. L., (List continued on next page.)

OTHER PUBLICATIONS

Polinsky, R. J., Nee, L., Foncins, J-F., Neve, R. L., McClatchey, A. I., Conneally, P. M., Gusella, J. F. The genetic defect in familial Alzheimer's disease is not tightly linked to the amyloid beta–protein gene. Nature 329:156–157 (1987).

Van Broeckhoven C., et al., Failure of familial Alzheimer's disease to segregate with the A–4 amyloid gene in several European families. Nature 329: 153–157, 1987.

Abrahm, C. R., et al., Cell 52, 487 (1988).

Sheng, M., and M. E. Greenberg. The regulation and function of c–fos and other immediate early genes in the nervous system. Neuron 4, 477 (1990).

Salbaum, J. M., Weidemann, A., Lemarie, H–G., Masters, C. L., Beyreuther, K. The promotor of the Alzheimer's disease amyloid A4 precursor gene EMBO J. 7, 2807 (1988).

Ruppert, C., and W. Willie, Molec. Brain Res. 2, 51 (1987).

Dragunow, M., and H. A. Robertson, Brain Res. 455, 295 (1988).

Zhang, P., et al., Neuroscience 46, 9 (1992).

Ellis, R. J., Annu. Rev. Biochem. 60, 321 (1991).

I. R. Brown, J. Neurosci. Res. 27, 247 (1990).

Jordan, S. A., McWilliams, P., O'Briain, D. S. and Humphries, P. Dinucleotide repeat polymorphism at the D14S42 locus. Nucl. Acids Res. 19, 1959 (1991).

Long, G. L., et al., Biochemistry 23, 4828 (1983).

Cox, D. W., et al., Nature 316, 79 (1985).

Nukiwa, T., et al., J. Hum. Genet. 43, 322 (1988).

Nukiwa, T., et al., J. Biol. Chem. 261, 15989 (1986).

Sharma, V., et al., Dinucleotide repeat polymorphism at the D14S43 locus. Nucl. Acids Res. 19: 1722 (1991).

Weber, J. L., et al., Mapping of human chromosome 5 microsatellite DNA polymorphisms. Genomics 11: 695–700 (1991).

Wang, Z., and J. L. Weber. Continuous linkage map of human chromosome 14 short tandem repeat polymorphisms. Genomics 13: 532–536 (1992).

Ostrander, E. A., et al., Construction of small–insert genomic DNA libraries highly enriched for microsatellite repeat sequences. Proc. Natl. Acad. Sci. (USA) 89:3419–3423, 1992.

Weber, J. L., and P. E. May. Abundant class of human DNA polymorphisms which can be typed using the polymerase chain reaction. Am. J. Hum. Genet. 44: 388–396, 1989.

Schellenberg, G. D., Kamino, K., Wijsman, E., Heston, L., Orr, H., White, J., Payami, H., Ball, M., Kaye, J., Warren, A., McInnis, M., Antonarakis, S., Martin, G. M., Bird, T. Neurobiol. Aging 13, suppl. 1, S67–68.

Wyman, A. R., and R. White. A highly polymorphic locus in human DNA. Proc. Natl. Acad. Sci. 77:6754–6758, 1990.

CHROMOSOME 14 AND FAMILIAL ALZHEIMERS DISEASE GENETIC MARKERS AND ASSAYS

This invention was made with government support under grant AG08017 awarded by the National Institute on Aging and grant R01MH43240 awarded by the National Institute of Mental Health. The government has certain rights in the invention.

FIELD OF THE INVENTION

The invention relates to gene probes and molecular genetic assays for early detection of Alzheimer's disease, as well as for identifying individuals who are at an increased relative risk of developing the disease.

BACKGROUND OF THE INVENTION

Alzheimer's disease (AD) is a progressive neurodegenerative disorder which in some (if not all) cases is inherited as an autosomal dominant trait. The first symptoms of AD can occur as early as the fourth to fifth decades of life. Alzheimer's disease is a major disease affecting over 3 million individuals in the U.S. alone at an annual cost of over $30 billion.

AD is characterized by progressive senile dementia with progressive loss of memory and motor functions. Prominent neuropathic features of AD include amyloid plaques, neurofibrillary tangles, and cerebral vascular amyloid deposits. Patterns of early-onset and late-onset AD have been reported in family inheritance studies. Analysis clearly indicates that AD is genetically heterogeneous. Numerous families have been described in which early-onset AD (onset <60 years) appears to segregate as an autosomal dominant trait (1-8; see the appended Citations). Since onset of AD is rare in the fourth and fifth decades of life, familial clustering over multiple generations is unlikely to occur by chance. In one subset of early-onset familial AD (FAD) kindreds, mutations at codon 717 of the amyloid precursor protein (APP) gene are responsible for the disease (9, 10). Alison Goate, John Hardy, and co-workers (9) identified a single base change in codon 717 of the APP gene. Subsequently it was reported that this substitution in one mutation is responsible for an early-onset FAD in 2 kindreds. Shortly thereafter, Murrell et al. (11) and Chartier-Harlin et al. (10) identified two additional FAD mutations in the same APP codon. These mutations suggest that APP and deposition of the $\beta$-peptide found in amyloid ($\beta$A4) are central to certain AD disease processes. A total of 4 APP mutations causing $\beta$A4 deposition have been identified: One at codon 693 which causes hereditary cerebral hemorrhage with amyloidosis of the Dutch-type (HCHWA-D; 10A), and three at codon 717 which cause FAD. These mutations are all found in exon 17 which, along with exon 16, encode the $\beta$A4 peptide. The HCHWA-D mutation is a gln→gly mutation associated with $\beta$A4 amyloid deposition (8). Despite the encouraging findings that APP mutations may be responsible for disease in certain families, it is now clear that these mutations are not associated with disease in the majority of FAD families with a high frequency of early-onset disease, including Volga German (VG) kindreds (17-21). In addition, FAD in most if not all late-onset kindreds does not appear to be associated with APP mutations (8,18,22). Thus, mutations in other as yet unidentified chromosomal locations may result in AD.

The role of inheritance in the more common late-onset AD is not presently resolved. Evidence that defective genes may be responsible for some or possibly all late-onset AD has been suggested by clustering of late-onset cases in individual pedigrees (8,14,22), family history data from case-control studies (23-26), and the concordance rates for mono- and di-zygotic twins (27-29). Certain data also suggest the possibility of "sporadic" AD, i.e., where no family history of disease is observed, that could result, for example, from noninherited genetic mechanisms such as somatic recombination or mutation.

The observation that APP mutations account for only a fraction of FAD confirms the hypothesis that the familial form of this disease is genetically heterogeneous (30,31). Evidence has been reported which suggests that an early-onset AD locus may exist on chromosome 21 that is centromeric to the APP gene (4,32). A late-onset AD locus has also been reported on chromosome 19 (14,33). However, many early-onset families do not map to chromosome 21 (8,18,22,34) or to chromosome 19 (14,37).

Two lines of evidence suggest that chromosome 19 may contain an FAD locus. First, a genetic association between FAD and an allele of a TaqI RFLP polymorphism was described by the present inventors at the Apo CII gene located at 19 q13.2 (12). The families analyzed were both early- and late-onset kindreds. Reevaluation of the Apo CII locus using a larger set of families (13) confirmed a statistically significant association between the locus and FAD, but the results of linkage analyses failed to show such an association in early-onset families and showed only a weak association (i.e., low positive LOD scores) with late-onset kindreds. The apparent conflict between the results of these two different analytic methods may indicate that a genetic model other than autosomal dominant inheritance may need to be applied to explain the genetic mechanisms operative in this type of AD.

The second line of evidence suggesting a chromosome 19 FAD locus comes from the work of Pericak-Vance et al. (14) who analyzed late-onset kindreds and reported statistically significant affected pedigree member results for BCL3 (a B cell chronic lymphocytic leukemia/lymphoma marker) and ATP1A3 (a subunit of the Na/K ATPase) at a significance level of p<0.01. Both of the latter markers are located on chromosome 19 at q13.1-13.2 and are proximal to Apo CII. Two-point LOD scores for these loci and others in the region were suggestive of linkage of the disease with this region of chromosome 19, but the values did not reach a level of statistical significance. When early-onset (instead of late-onset) families were analyzed, the LOD scores were negative and the APM results were also not statistically significant. Multipoint genetic linkage analysis suggested a possible localization of an FAD gene locus in the vicinity of BCL3 and ATP1A3. A peak position score of over 4.0 was achieved when late-onset families were analyzed at the 1% penetrance level. In summary, although substantial evidence exists for a possible late-onset FAD locus in the vicinity of Apo CII and BCL3 on chromosome 19, this putative locus does not appear to be related to the genetic disease observed in early-onset AD families.

Relatively few markers have been described for chromosome 14, and the maps that have been described show genetic markers clustered within the proximal and distal portions of the q arm with an unconnected gap between the clusters. No polymorphisms have been mapped in the short arm of this acrocentric chromosome although a genetic map has recently been constructed using dinucleotide repeat polymorphic markers (56). Dinucleotide repeat polymorphism has also been reported in chromosome 14 marker D14S43 (55). No AD or FAD gene locus has previously been reported to be associated with chromosome 14.

At present there is no reliable method for presymptomatic or prenatal diagnosis of genetic predisposition for Alzheimer's disease. The search for additional genetic markers linked to AD has proven difficult because of the late age of onset and subsequent need for a large number of families and subjects for typing. Thus, while it may have appeared likely that at least one other AD locus remains to be identified, the existence of such a locus has not been reported.

SUMMARY OF THE INVENTION

To identify chromosomal regions harboring familial Alzheimer's disease genes, the genome was searched using linkage analysis. Surprisingly, a marker selected at random as a marker for chromosome 14, i.e., D14S43, gave highly significant positive LOD scores in early-onset non-Volga German AD (ENVG) kindreds: a $Z_{max}$ value of 9.15 ($\Theta=0.01$ using an age-dependent penetrance function) was obtained with D14S43 at 14 q24.3. Results for control Volga German AD families (i.e., without AD) were either negative or nonsignificant for markers in the q24.3 region of chromosome 14. Thus, the results indicate a previously unrecognized familial Alzheimer's disease locus is present on chromosome 14.

The chromosome 14 AD locus was mapped in ENVG kindreds, and the locus was isolated to the region between karyotypic bands q11.2 and q32.1. These band regions contain, respectively, the D14S47 and D14S48 markers, and the q11.214 q32.1 region encompasses the D14S42, D14S43, D14S52, and D14S53 markers. The chromosome 14 AD locus showed the greatest calculated correspondence with the q24.3 region of chromosome 14 containing the D14S43 and D14S53 markers.

Localization of the novel Alzheimer's disease locus to a region between the q11.2 and q32.1 bands of chromosome 14, and the identification of closely-linked genetic markers between the D14S47 and D14S48 markers, make available assays for identifying individuals carrying genetic markers closely linked with the chromosome 14 AD locus and thus having predisposition for developing the disease.

DETAILED DESCRIPTION OF THE PREFERRED EMBODIMENT

The experimental results presented below describe the discovery of a new genetic variant of Alzheimer's disease (AD) that has a disease phenotype closely linked to genetic markers in the region of chromosome 14 between the q11.2 and q32.1 bands that is bounded by the D14S47 and D14S48 dinucleotide repeat genetic markers. This new genetic variant of AD is termed herein chromosome 14-AD, and the genetic markers for this disease are termed herein chromosome 14-AD markers. The most closely linked genetic markers map between D14S47 and D14S48 into a region between a proximal D14S52 marker and a distal D14S53 marker, and the most closely linked marker identified to date in the latter region is D14S43. Linkage of D14S43 with AD is extremely strong, with a highly significant 2-point LOD score of >9. Identification of closely linked markers for a chromosome 14-AD gene locus in the q11.2–q32.1 region is a major step in resolving the complex genetics of familial Alzheimer's disease. The identification of a chromosome 14-AD gene linked to the markers in this region should prove extremely useful in resolving the pathogenetic pathways leading to the development of AD and in devising treatment of chromosome 14 AD defects.

Figure 1:
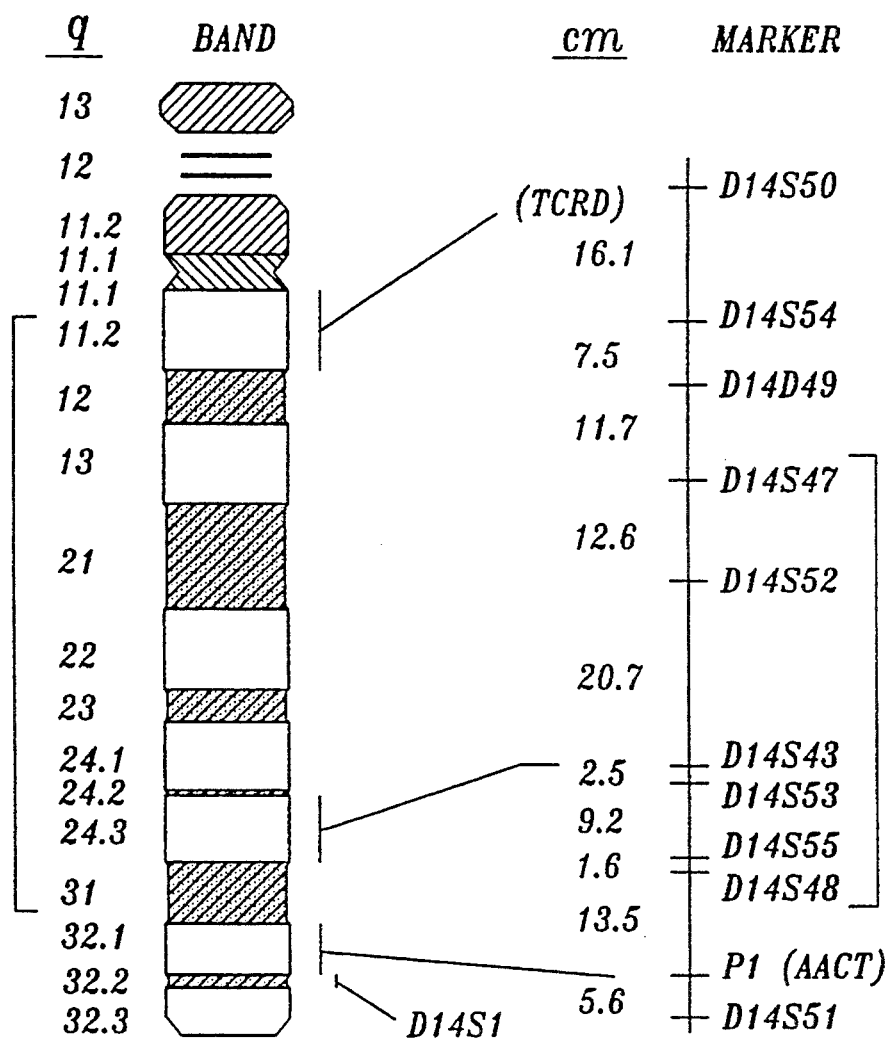
FIG. 1 depicts the band markers ("q") and location of dinucleotide repeat genetic probe markers ("D14S") on chromosome 14. This genetic map was constructed using the CEPH families and the computer program CRIMAP (26). Band positions (q) are identified on the left, and distances between the D14S dinucleotide repeat markers are given in centimorgans (sex-averaged; cm) on the right using the Kosombi map function. The order for D14S53-D14S43 was favored over the reverse order by a likelihood ratio of 7700:1. The order for loci D14S48-PI-D14S51 was favored by $10^{12}$:1 odds. Band locations were determined by others (42).

The results disclosed herein demonstrate the existence of one or more previously unrecognized familial Alzheimer's disease genes in the DNA of chromosome 14, termed herein chromosome 14 AD loci. The present discovery isolates the chromosome 14-AD loci through its linkage to closely linked markers that are resident between bands q11.2 and q32.1 of chromosome 14, as shown in FIG. 1. The polymorphic genetic markers that bound the subject region between the q11.2 and q32.1 bands are dinucleotide repeat sequence markers D14S47 and D14S48. The latter markers (and others) were identified using specific oligonucleotide primers to amplify polymorphic DNA "allelic" variants resident within this region of genomic chromosome 14 DNA in Alzheimer's disease patients and their family members. Within a family having a chromosome 14-AD, one or more of the DNA allelic variants co-segregates with and is linked closely with the Alzheimer's disease phenotype in the family.

Abbreviations used herein include: $\Theta$, recombination fraction; $A\beta$, the $\beta$-peptide found in amyloid; AACT, $\alpha_1$-antichymotrypsin gene; AD, Alzheimer's disease; APP, amyloid precursor protein; cm or cM, centimorgan; cR, centiray; ENVG, early-onset (i.e., $\leq 60$ years of age) non-Volga German; EST, expressed sequence tag; FAD, familial Alzheimer's disease; FISH, fluorescent in situ hybridization; Gm, the immunoglobulin heavy chain gene cluster; LOD, logarithm of the odds ratio; Mb, megabase; PFGE, pulse-field gel electrophoresis; PI, $\alpha_1$-antitrypsin gene; PIC, polymorphic information content; PI/AACT, the gene region encompassing both PI and AACT; PCR, polymerase chain reaction; POLB, DNA polymerase $\beta$; R, ray; RFLP, restriction fragment length polymorphism; RH, radiation-hybrid, i.e., of a radiation-reduced somatic cell hybrid; SSCA, single-strand sequence analysis; STRP, short tandem repeat polymorphism, (i.e., in genetic markers such as D14S43 and TCRD); STS, sequence tagged site; TCRD, T cell receptor domain gene locus; VG, Volga German; YAC, yeast artificial chromosome; and, 14 q11.2 to 14 q32.1 or q11.2–q32.1, the region between chromosomal bands q11.2 and q32.1 as depicted in FIG. 1.

As used herein the terms below are intended to have the following meanings: "Association" is used to mean that the subject genetic marker is always found with the phenotype of Alzheimer's disease in all the individuals in all of the respective families having a member with a chromosome 14-AD. A chromosome 14-AD locus is an example of a genetic marker that exhibits such an association with an Alzheimer's disease phenotype in a chromosome 14-AD.

"Marker" is used herein to refer to a nucleotide sequence that is present in genomic DNA identifiable with specific oligonucleotide probes (e.g., in genomic fragments of DNA having distinguishably different physical attributes such as size) in the DNA of different individuals in a human population. Representative examples of markers include genes, transcription regulatory elements, repetitive sequence motifs, i.e., short and long tandem repeat sequences (SLTR; di, tri, and longer repeated sequences), and the like.

"Polymorphism" is intended to mean that a subject marker can be found in distinguishably different physical forms (e.g., size, charge, nucleotide sequence) in genomic DNAs obtained from different individuals in a human population.

The term "nucleic acid" is used herein to refer to natural or synthetic + and/or −strands of DNA, RNA, polynucleotides (i.e., greater than three nucleotides), and synthetic or natural oligonucleotides (i.e., greater than nine nucleotides), including antisense RNA and oligonucleotides.

The term "capable of specifically hybridizing" is used interchangeably with the term "capable of hybridizing under stringent conditions" herein to mean that members of the subject group of nucleic acids may be readily identified by their ability to hybridize under stringent conditions with all or parts of an isolated DNA segment that contains a genetic marker gentically linked and co-segregating with an Alzheimer's disease trait in a family (i.e., the genetic marker is indicative of the disease trait in the family). Isolated DNA segments consist of nucleotide sequences that, in turn, may be used to construct (or isolate) a variety of nucleic acid molecules (i.e., cDNA, RNA, synthetic and natural polynucleotides, oligonucleotides, antisense oligonucleotides, and the like). Nucleic acids that are members of the subject group of molecules are rapidly identified by their common capacity to hybridize under stringent conditions with the subject isolated DNA segment containing the indicative genetic marker for a chromosome 14 Alzheimer's disease trait in a family. The nucleic acid molecules that are so capable of hybridization commonly contain a nucleotide sequence that is complementary with at least one helical turn (about 10 to 15 nucleotides) of a + or −strand of the subject isolated DNA segment. By capable of hybridizing under stringent conditions it is meant that annealing the subject nucleic acid with at least a region of a genetic marker occurs under standard conditions, e.g., high temperature and/or low salt content, which tend to disfavor hybridization of noncomplementary nucleotide sequences. A suitable protocol (involving $0.1 \times SSC$, 68° C. for 2 hours) is described in Maniatis, T., et al., *Molecular Cloning: A Laboratory Manual*, Cold Springs Harbor Laboratory, 1982, at pages 387–389. Such hybridizing nucleic acid molecules may be related to the disclosed sequences by deletion, point mutation, base substitution, frameshift, alternative ORFs, mRNA splicing and processing, or post-transcriptional modification (e.g., methylation and the like).

The term "nucleotide sequence" is used herein to refer to a sequence of nucleosides or nucleotides and may include non-contiguous sequences (e.g., in genomic sequences exon coding region sequences may be interrupted by intron sequences).

The term "contiguous nucleotide sequences" is used herein to refer to a sequence of nucleotides linked in a serial array, one following the other.

The term "PCR" is used herein to refer to the process of amplifying DNA segments through the use of a DNA template molecule, 2 oligonucleotide primers, and a DNA polymerase enzyme. The DNA template is dissociated at high temperature from primers that may be annealed to the template. The DNA polymerase copies the template starting at the primers. The process is repeated 30–40 times to amplify and enrich the template-specific molecules in the reaction product.

"Alzheimer's disease" is used herein interchangeably with the acronym "AD" to refer to clinical disease characterized by a dementia with progressive loss of memory and motor functions that is characterized by the following neuropathic phenotypic features: amyloid plaques, neurofibrillary tangles, and cerebral vascular amyloid deposits in the brain. The chromosome 14-AD described herein is further characterized in family inheritance studies by a familial association primarily with patterns of early-onset (before or at age 60) but also some individuals in certain families that have a late-onset (after age 60).

"Alzheimer's disease phenotype" is intended to mean one or more clinical criteria, characteristics, or results of diagnostic procedures used to diagnose a patient as having Alzheimer's disease.

"Alzheimer's disease trait" is intended to mean a genetic characteristic resident in the genome of an individual that may or may not be expressed as a phenotype in the individual. An Alzheimer's disease phenotype is an example of expressed Alzheimer's disease trait.

"Early-onset FAD" refers to familial-linked Alzheimer's disease with an onset prior to or at 60 years of age.

"Late-onset FAD" refers to familial-linked Alzheimer's disease with an onset after age 60.

"Sporadic AD" refers to Alzheimer's disease without a heritable genetic association.

"Chromosome 14-AD gene locus (or loci)" is used herein to identify one (or more) clustered genetic loci located within a unique region of chromosome 14 between bands q11.2 and q32.1 and delineated by close genetic linkage and co-segregation with genetic markers between D14S47 and D14S48 as illustrated in Table 1, below. In an illustrative example, the D14S genetic markers of Table 1 are assayed using PCR primers (shown as SEQ. ID. NOS. 1–12 in Table 1) and PCR amplification methods to expand and identify the different respective 50–200 bp regions of chromosome 14. The subject chromosome 14-AD gene loci are not detectable in chromosome 19 or chromosome 21.

"q11.2–q32.1 region of chromosome 14" is used herein to mean the region of chromosome 14 between band q11.2 and band q32.1 that is bounded at one end by a D14S47 genetic marker and at the other end by a D14S48 genetic marker. The D14S47 and D14S48 genetic markers are both dinucleotide repeat genetic markers. The subject q11.2–q32.1 region contains the D14S42, D14S43, D14S52, and D14S53 markers that are conveniently identified using the designated oligonucleotide probes shown in Table 1.

"q24.3 region of chromosome 14" is used herein to mean the q24.3 band of chromosome 14 that may be visualized in karyotyped DNA by cytogenetic methods.

"Genomic library," "genomic DNA library," "DNA library," and "chromosome 14 library" are intended to mean a collection of clones of host cells each having a segment of genomic DNA.

"Genetic marker indicative of a chromosome 14-AD" and "indicative genetic marker" are used interchangeably herein to refer to genetic markers that are genetically linked and co-segregate with an Alzheimer's disease phenotype in a family, e.g., as DNA allelic variants of the genetic markers that are detectable in fragmented genomic DNA samples (or PCR regions) isolated from members of a family containing one member with a chromosome 14 AD trait (e.g., a chromosome 14 AD proband). The genetic marker that is closely linked with a chromosome 14-AD gene locus in the family is inheritable as a unit having limited recombination with the Alzheimer's disease trait in the family. The pattern of inheritance observed is one in which one or more allelic variants (i.e., alleles) of the genetic marker co-segregate with the chromosome 14-AD trait in the family, and are gentically linked with the trait in the family such that the linkage observed has an LOD score of at least 3 at a recombination fraction of about 0.0 to about 0.1. Examples of chromosome 14-AD markers with allelic variants co-segregating with Alzheimer's disease are shown in FIGS. 2A–2B and 3A–3G. Illustrative examples of chromosome 14-AD genetic markers within the q11.2–q32.1 region that are bounded by the D14S47 and D14S48 markers include the following: short tandem repeat polymorphism (STRP; e.g., such as described in citations 62–65); restriction fragment length polymorphic (RFLP) sites; variable number of tandem repeat (VNTR) markers (including repeat lengths as short as 2 base pairs such as D14S43 and markers having longer repeat lengths such as D14S1); insertion or deletion polymorphisms; and single base variants not occurring at restriction enzyme sites and thus not detectable by RFLP analysis. Other illustrative examples of the subject genetic markers include coding and noncoding regions of gene sequences identified by direct sequencing of genomic DNA from the subject q11.2–q32.1 region with the aid of computer-assisted gene identification and techniques such as GRAIL (72) or single strand conformation analysis (see Example 3, below). Other examples include novel RFLP markers, deletion/insertion sites, and long-allele (e.g. D14S1) polymorphic markers and the like which may be isolated as anonymous DNA fragments either from a genomic library (71) or from a commercially available chromosome 14 flow-son library (see Example 3).

"Co-segregation" is used to mean that a specific allele of one polymorphic locus (e.g., a genetic marker allelic variant) is inherited together, within a human family, with a specific allele of another locus (e.g., an Alzheimer's disease trait). Co-segregation occurs when the 2 loci are on the same chromosome and located physically close enough so that the rate of genetic recombination between the two loci is low or zero. Co-segregation of genetic markers was first discovered by Mendel in the 19th century and is the basis of all modern genetics. It is now known that two loci co-segregating in a statistically significant manner (typically determined by linkage analysis and by determining an LOD score statistic, as described below) are: a) located on the same chromosome, b) located in the same contiguous stretch of DNA, and c) located physically close to one another, typically within 50 million base pairs or less. Co-segregation of the subject genetic marker and a chromosome 14-AD trait may conveniently be observed in certain families by analyzing the pedigree of the allelic variants of the genetic marker in the genotypes of the different family members. For example, if a father has alleles A and B at locus 1 and C and D at locus 2, and the mother has alleles E and F at locus 1 and G and H at locus 2, the pair of loci are said to co-segregate if, among the children, the A allele is consistently inherited from the father and observed with only the C or D allele. Alternatively, if all children that inherit the A allele always inherit the C allele, locus 1 and locus 2 would be said to co-segregate. In another example, in a different family with parents having the same AB and CD genotypes, if the children who inherited A consistently inherit D, and other children who inherit B consistently inherit C, then locus 1 and 2 are again said to co-segregate. Co-segregation may also be observed by statistical analysis of the inheritance patterns of alleles in families, as described in greater detail below. The D14S43, D14S53, D14S52, and D14S42 genetic markers described in Examples 1 and 2 are illustrative of genetic markers that co-segregate with the chromosome 14-AD trait in ENVG families, and are closely linked and co-segregating in these families with an early-onset AD phenotype and chromosome 14-AD gene locus.

"Linkage" is used to mean that the subject marker may be genetically linked with the chromosome 14-AD trait in certain familieors that the marker and the trait are linked in all families. A marker and a chromosome 14-AD gene locus are said to be linked (one to the other) if the marker and the locus co-segregate in certain families as determined by pedigree analysis (discussed above) or genetic linkage analysis and statistical probability calculations as discussed below. Examples of families in which chromosome 14-AD genetic markers co-segregate with a chromosome 14-AD trait are described in Example 1 and Table 3. Statistically, linkage may be described as the probability that two different genetic markers (or that a genetic marker and a chromosome 14-AD trait or phenotype) are linked, and this probability is expressed as a statistic termed an "LOD score at a selected recombination fraction." Linked loci have a maximal value for the LOD score at a particular recombination fraction, and this is termed herein the "maximal LOD score." An LOD score of 3 or greater is statistically significant evidence of linkage between a pair of genetic markers, or a marker and a chromosome 14-AD trait, within the particular population under examination. An LOD score of less than $-2$ (minus 2) is considered statistically significant evidence that a pair of markers, or a marker and a disease phenotype (or trait), are not linked and are not co-segregating in the population under examination.

"Linkage analysis" is intended to have its conventional meaning as a method of genotyping polymorphic markers in human families, observing co-segregation, and analyzing the resulting data by statistical methods such as the LOD score method described below.

Figure 2A:
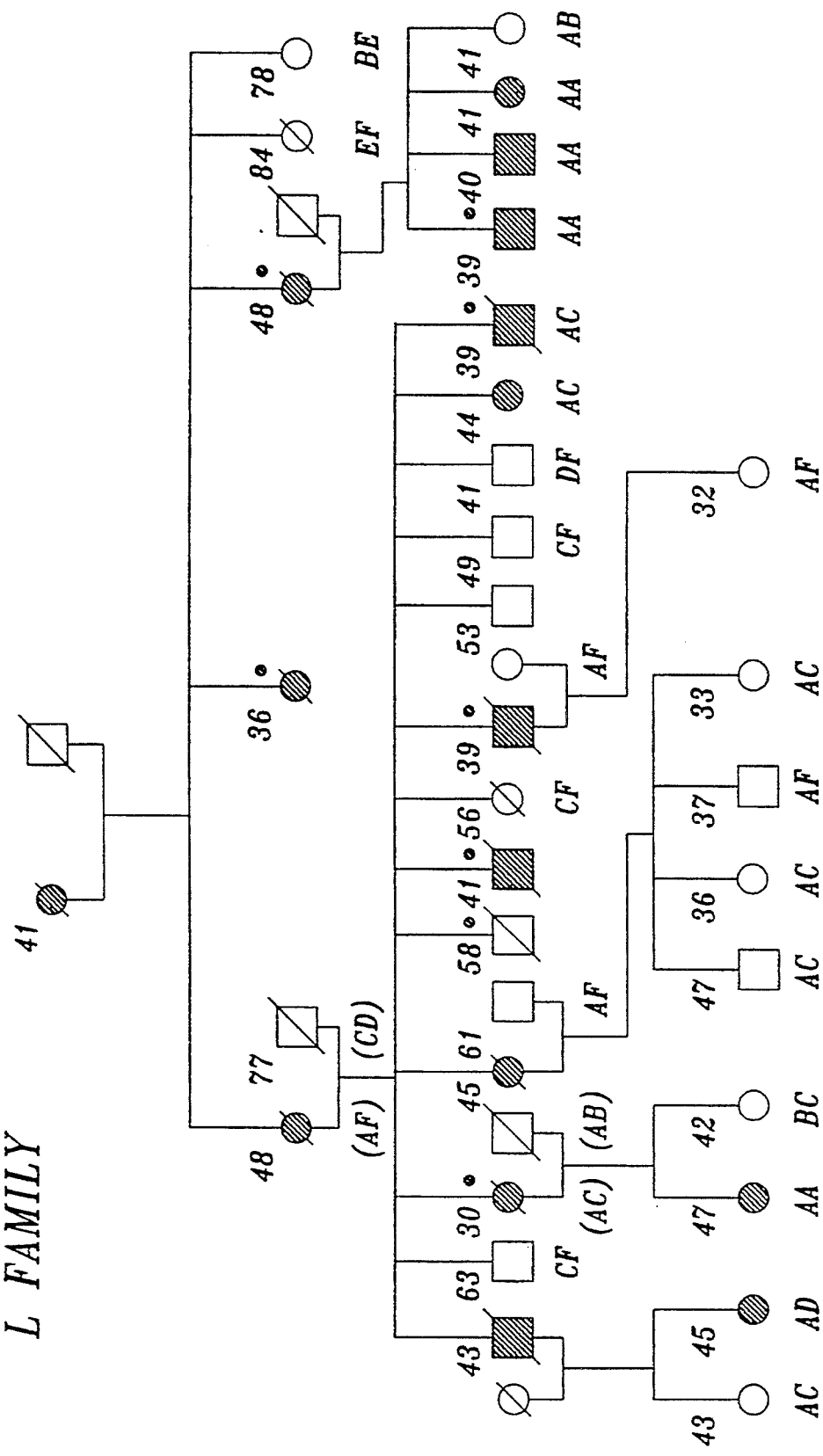
FIGS. 2A and 2B shows the pattern of segregation for the D14S43 chromosome 14 AD marker alleles in FAD Families L (FIG. 2A) and SNW (FIG. 2B). Alleles are shown below subjects and were recoded as follows: A, 159 bp; B, 179 bp; C, 181 bp; D, 183 bp; E, 185 bp; F, 187 bp; and G, 175 bp. Genotypes in parentheses were deduced from spouse and offspring genotypes. Solid symbols represent affected subjects; and a slash indicates the subject is deceased. The number above and to the left of subjects is the age-of-onset for affected subjects, the current age for living subjects, or the age at death for unaffected subjects. For affected subjects, if the age-of-onset is not known, the age of death is shown preceded by "D". A dot above and to the right of a subject indicates an autopsy was performed. One non-demented subject in the L family was autopsied and found to be neuropathologically normal.
Figure 2B:
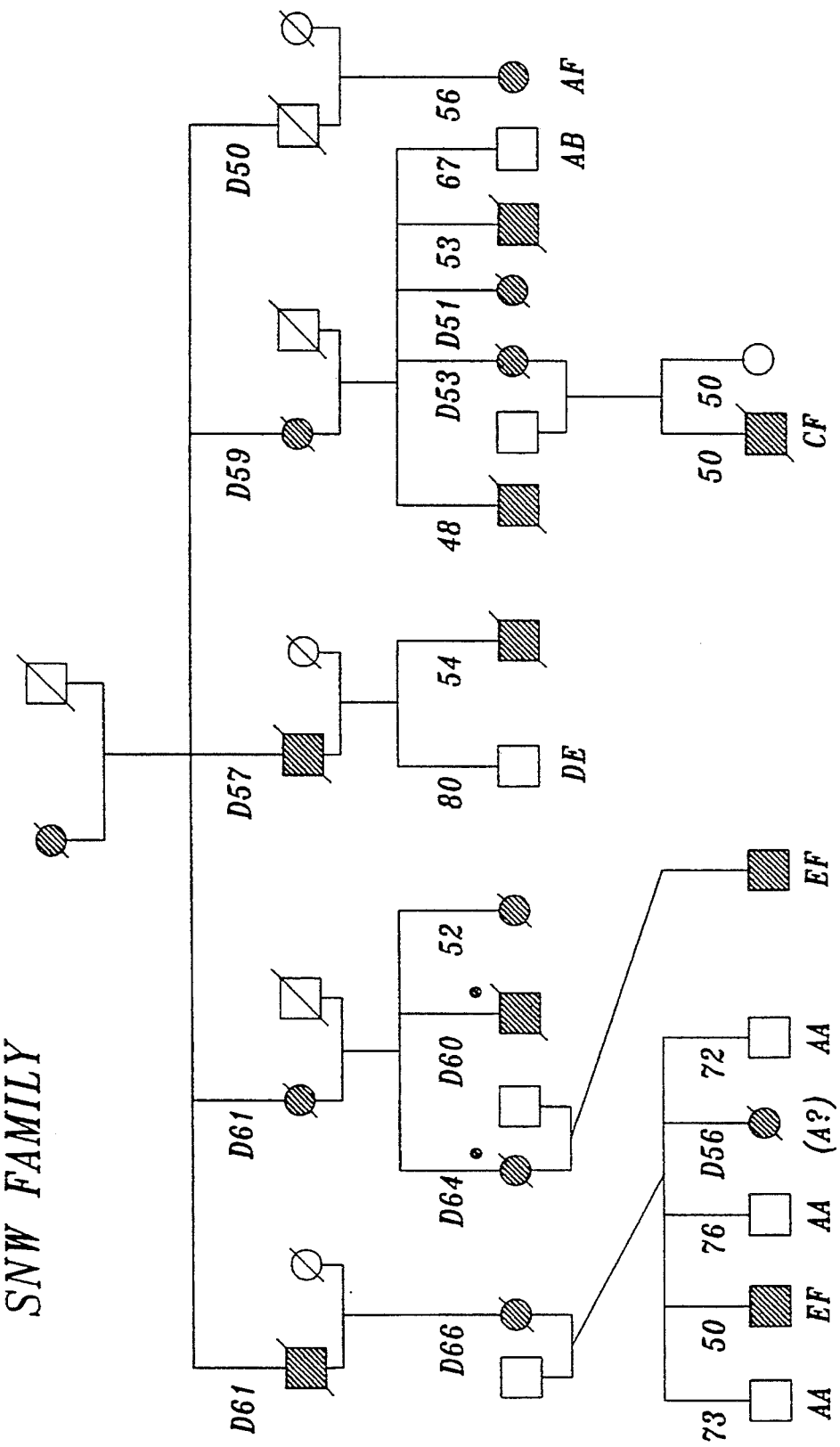
Figure 3A:
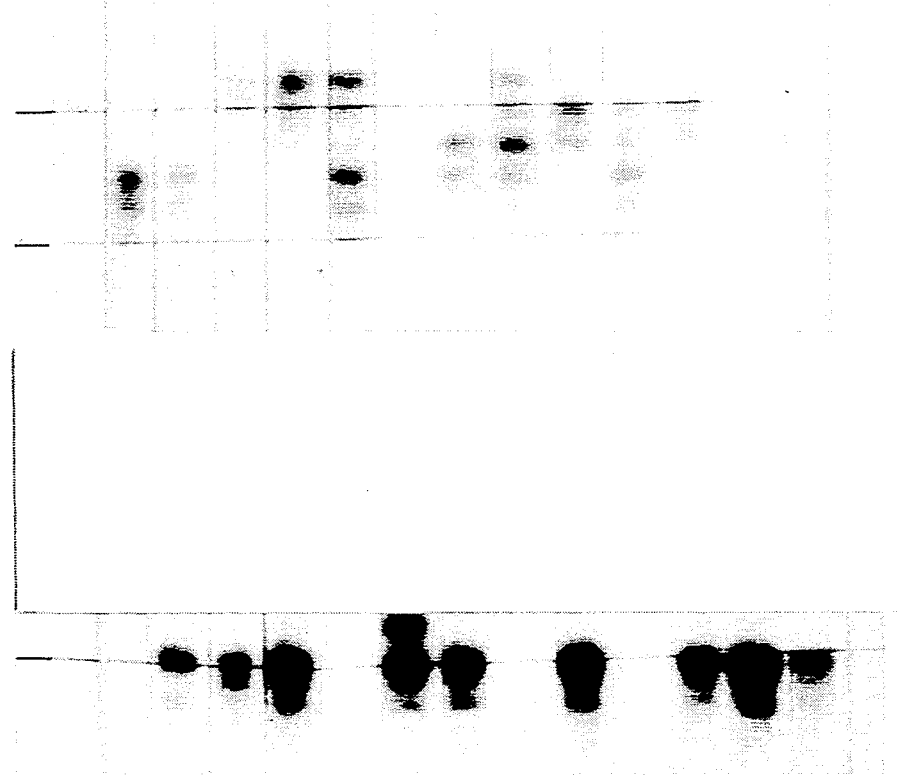
FIG. 3A shows the pattern of D14S43 chromosome 14 Alzherimer's disease genetic marker alleles amplified from genomic DNA by PCR and isolated by polyacrylamide gel electrophoresis. The major alleles for each subject are shown in the respective lanes of the gel as "#/#", e.g., 159/189, and the following alleles were recorded: A, 159 bp (lanes 4,5,7,8,12,13); D, 183 bp (lanes 6,11); E, 185 bp (lanes 8,9); F, 187 bp (lanes 10–12); H, 161 bp (lane 7); and I, 189 bp (lanes 3,4,5,9).
Figure 3B:
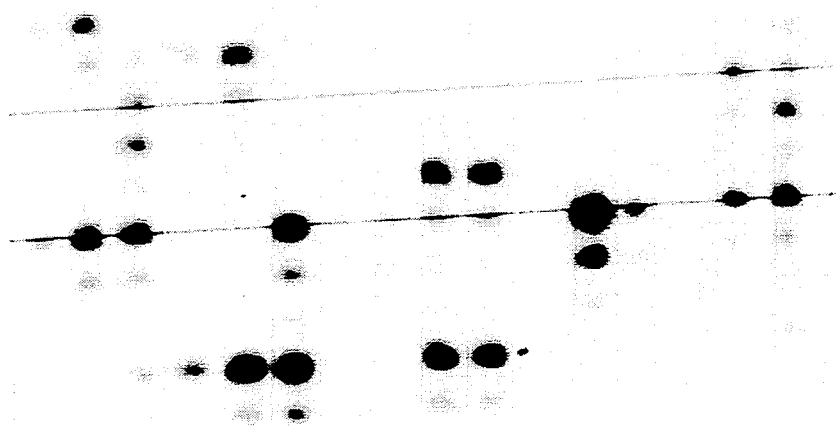
FIG. 3B shows the pattern of D14S42 chromosome 14 Alzherimer's disease genetic marker alleles amplified from genomic DNA by PCR and isolated by polyacrylamide gel electrophoresis. The major alleles for each subject are shown in the respective different lanes of the gel as "#/#", e.g., 121/131, and the following alleles were recorded: A, 115 bp (lanes 5–7,11); B, 121 bp (lane 11); C, 123 bp (lane 11); D, 129 bp (lanes 5,6,9); and E, 131 bp (lane 3).
Figure 3C:
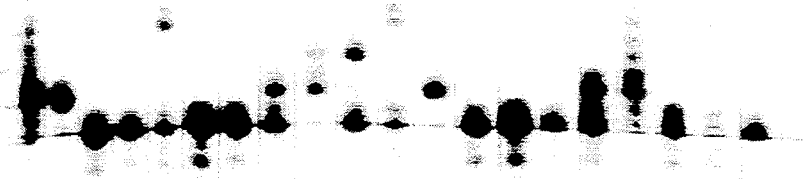
FIG. 3C shows the pattern of D14S47 chromosome 14 Alzherimer's disease genetic marker alleles amplified from genomic DNA by PCR and isolated by polyacrylamide gel electrophoresis. The major alleles for each subject are shown in the respective different lanes of the gel as "#/#", e.g., 75/77, and the following alleles were recorded: A, 75 bp (lanes 3–8, 10–11, 13–16, 18–21); B, 77 bp (lanes 2,9,12,16,21); C, 79 bp (lanes 9,10); D, 81 bp (lanes 5,11,19); and, E 83 bp (lane 15).
Figure 3D:
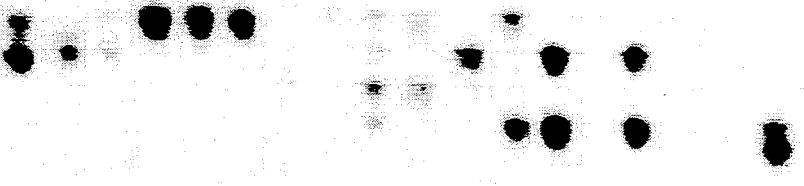
FIG. 3D shows the pattern of D14S48 chromosome 14 Alzherimer's disease genetic marker alleles amplified from genomic DNA by PCR and isolated by polyacrylamide gel electrophoresis.
Figure 3E:
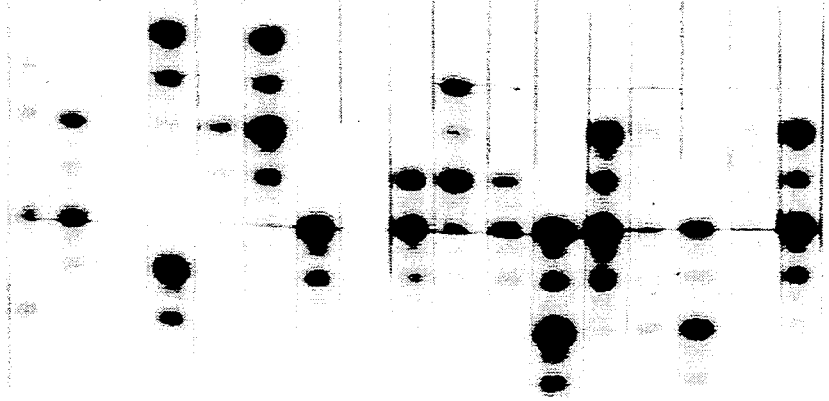
FIG. 3E shows the pattern of D14S52 chromosome 14 Alzherimer's disease genetic marker alleles amplified from genomic DNA by PCR and isolated by polyacrylamide gel electrophoresis. The major alleles for each subject are shown in the respective different lanes of the gel as "#/#", e.g., 81/91, and the following alleles were recorded: A, 79 bp (lanes 12,15); B, 81 bp (lane 4); C, 83 bp (lanes 7,9,10–13,15,16); D, 85 bp (lanes 9,11); E, 87 bp (lanes 5,6,13,16); F, 89 bp (lane 10); and G, 91 bp (lanes 4,6).
Figure 3F:
FIG. 3F shows the pattern of D14S53 chromosome 14 Alzherimer's disease genetic marker allels amplified from genomic DNA by PCR and isolated by polyacrylamide gel electrophoresis. The major allels for each subject are shown in the respective different lanes of the gel as "#/#", e.g., 151/159, and the following alleles were recorded: A, 144 bp (lane 12); B, 149 bp (lanes 3,4); C, 151 bp (lanes 1,2,4,5,8–11, 13–15); D, 155 bp (lanes 8–13); E, 157 bp (lane 14); and F, 159 bp (lane 1–3).
Figure 3G:
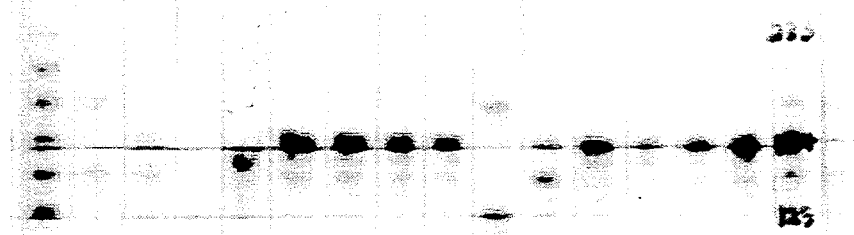
FIG. 3G shows the pattern of D14S55 chromosome 14 Alzherimer's disease genetic marker alleles amplified from genomic DNA by PCR and isolated by polyacrylamide gel electrophoresis. The major alleles for each subject are shown in the respective different lanes of the gel as "#/#", e.g., 125/129, and the following alleles were recorded: A, 123 bp (lanes 3,10); B, 125 bp (lanes 1,2,11,17); C, 127 bp (lanes 2-9, 11-15); and D, 129 bp (lanes 10, 17).

"Isolated DNA segment" is used herein to refer to a DNA fragment, such as a PCR region or an SLTR or RFLP fragment, that can be prepared from the genomic DNA of an individual in a human population and that contains a genetic marker indicative of a chromosome 14-AD trait in a family and having a maximal LOD score at a recombination fraction of about 0.0 to about 0.1. Illustrative examples of genetic markers indicative of a chromosome 14-AD trait in a family are provided by the "DNA allelic variants", "alleles" and "chromosome 14-AD marker alleles" described in the Examples; the three latter terms are used interchangeably to refer to genetic markers gentically linked and co-segregating with a chromosome 14-AD trait in a family. In this context, the subject "isolated DNA segment" refers to nucleic acid that contains the nucleotide sequence for one or more alleles that identify one or more DNA fragments that are closely linked with the chromosome 14-AD trait. Illustrative examples of isolated DNA segments include coding and noncoding regions of genomic DNA, RFLP fragments, SLTR fragments, PCR amplification products, and repetitive genomic DNA sequences (e.g., $(CA)_n$). The subject isolated DNA fragments may be identified by Southern blotting (e.g., for RFLP fragments) or by distinguishing the different numbers of repeat units for different repetitive alleles, e.g., SLTR fragments isolated as PCR products using polyacrylamide gel electrophoresis). The latter PCR method can separate and identify two different isolated DNA segments that consist of only a one base pair difference. D14S43 is an example of a marker with alleles that differ in the number of CA repeat sequences (FIGS. 2A, 2B, and 3A).

The term "chromosome 14-AD probe" is used to mean a natural or synthetic oligonucleotide having a nucleotide sequence capable of hybridizing under stringent conditions with a plus or a minus strand of a chromosome 14-AD marker DNA allelic variant. Illustrative examples of the subject chromosome 14-AD probes include the SEQ. ID. NOS. 1–12 oligonucleotides in Table 1.

"AD proband" is used herein interchangeably with "chromosome 14-AD marker proband" and "chromosome 14-AD proband" to refer to a propositus (male) or proposita (female) that is clinically affected with at least one Alzheimer's disease phenotype, and only to such a male or female whose genotype is useful for constructing a family pedigree showing segregation of a chromosome 14-AD marker DNA allelic variant with an Alzheimer's disease phenotype in the family. Skilled artisans in genetic counseling and human genetic diseases routinely identify probands so that suitable marker alleles can be selected for family testing. In practice, an AD proband is frequently identified as the family member suffering from clinical Alzheimer's disease who signals the possible existence of the chromosome 14-AD gene within a family. In such a case the genetic counselor desiring to obtain genetic information about the nature of the disease in the individual needs to determine whether the disease is linked to chromosome 21, 19, or 14. When the linkage of the disease in the clinically affected individual has been determined, and if that disease linkage is to a chromosome 14-AD marker, then the "signal" individual in the family may serve as the AD proband for genetic testing and couseling of other family members. In this process skilled artisans recognize that to determine disease linkage with a chromosome 14-AD marker it may be necessary to evaluate inheritance patterns of several different chromosome 14-AD markers and several of their DNA allelic variants in the genomic DNAs of members of the family and the clinically affected individual. It is not necessary in the present disclosure to detail methods commonly used in determining segregation patterns of human genetic diseases (for additional methodology in constructing pedigrees and the like the reader is directed to Vogel, F., and A. G. Motulsky, 1986, *Human Genetics: Problems and Approaches*, 2nd Edition, Springer-Verlag, NY). The individuals in a family who can provide information to determine co-segregation of an allele with an AD trait include: individuals in the family having an AD phenotype (e.g., the AD proband or others); unaffected healthy blood relatives of an individual with an AD trait; and spouses of both individuals with an AD phenotype and healthy family members who may or may not carry the chromosome 14 AD trait. FIG. 2 provides an example of the type of data that may be collected and analyzed to determine a pedigree and co-segregation of an Alzheimer's disease phenotype with chromosome 14-AD markers in a family.

"Genotype analysis" is used herein to refer to a method for determining the presence or absence of one or more DNA allelic variants of a chromosome 14-AD genetic marker in the genomic DNA prepared from an individual. In most cases there will be two major alleles for genes in genomic DNA, but for repetitive sequence elements (e.g., SLTRs and the like; as illustrated in FIGS. 3A-3G) there may frequently be 4 or 5 (or more) different DNA allelic variants of a marker, since recombination in repetitive regions appears to be more common.

"Pedigree" is used herein to refer to a family tree.

"Predisposition for developing Alzheimer's disease" as used herein in relation to a chromosome 14-AD genetic marker means that a presymptomatic individual with a chromosome 14-AD trait is at an increased risk of developing a chromosome 14-AD phenotype if the individual has a marker in his/her genomic DNA that is closely linked to the chromosome 14-AD gene loci in region q11.2–q32.1. It is routine in the art of genetic counseling to determine such risk factors given the presence of a closely linked molecular genetic marker in the genomic DNA of the individual and when combined with the additional understanding provided by the pedigree of the individual in the family. For example, a risk factor may be calculated for an individual in a chromosome 14-AD family in a manner similar to that described previously for assessing risk Huntington's disease (74) and cystic fibrosis (59) families.

"Linkage analysis" is used herein to refer to assays and calculations routine in human genetics for determining the statistical probability of linkage of one marker to another marker (e.g., an Alzheimer's disease phenotype or chromosome 14-AD marker) in the genomic DNA of an individual.

"LOD score" is used to mean an indicated probability (LOD score) that a DNA allelic variant of a chromosome 14-AD marker is linked with an Alzheimer's disease phenotype in a family at a particular distance from the chromosome 14-AD gene, i.e., within a recombinant fraction of individuals in the subject family. For example, a calculated LOD score of 3.0 at a recombinant fraction (RF) of 0.0 is used to mean that the subject marker has a statistical significance (p<0.05) of being linked relatively closely (i.e., 0.0) to the AD phenotype in the family at the level of 95% confidence. The maximum LOD score will occur at a specific RF value (e.g., 0.0 in the above example). The RF value at which the maximum LOD score occurs indicates the distance between two markers, e.g., the AD phenotype and the genetic marker. The smaller the RF value at the maximum LOD score, the closer the two markers are on a genetic map. For example, the CF gene has an LOD score for linkage with the cystic fibrosis phenotype of about 80 at an RF value of 0.0. LOD scores as developed by Haldane and Smith (1947), modified by Morton (37), and described by Vogel and Motulsky in 1986 (74) are generally used to assess linkage. The principle may be outlined as follows:

The probability $P_2$ that the observed chromosome 14-AD family data conform to the behavior of two independent unlinked loci (e.g., a chromosome 14-AD marker and an Alzheimer's disease phenotype) under full recombination is calculated. Next, the probability $P_1$ that the identical family data are the result of two linked loci under a specified recombination fraction ($\Theta$) is calculated. The ratio of the two probabilities is the likelihood ratio and expresses the odds for and against linkage of the marker loci with the chromosome 14-AD gene. The ratio is calculated for each available chromosome 14-AD family ($F_n$) using the following equation:

$$\text{Odds ratio for } F_n = [P_1(F/\Theta)]/[P_2(F/(\tfrac{1}{2}))]. \qquad 1.$$

For convenience, the logarithm of the ratio is commonly used, and an LOD score z (meaning "log odds" or "log probability ratio") is calculated from the equation:

$$z = \log_{10}[P(F/\Theta)]/P(F/(\tfrac{1}{2}))], \qquad 2.$$

where $P(F/\Theta)$ denotes the probability of occurrence for a family F when the recombination fraction is $\Theta$. The LIPED program is a well known (and used) computer program described in 1976 by Ott (Am. J. Hum. Genet. 28: 443–454) that calculates the maximum likelihood of linkage between two genes considering all pedigree data, and the result is expressed as a resultant likelihood of linkage = $Z_{max}$.

"Recombinant fraction" is used herein to mean that fraction of individuals in a family whose genotype indicate that they are recombinant for a DNA allelic variant of a chromosome 14-AD marker in relation to another marker (e.g., an AD phenotype or a second marker). For example, with perfect segregation, RF=0.0 would indicate that no recombination has occurred between the DNA allelic variant marker and the second marker (or phenotype), i.e., the two markers would segregate together because they are closely linked.

The invention provides isolated DNA segments carrying at least a portion of a genetic marker that is indicative of a chromosome 14 Alzheimer's disease trait in a family. The subject genetic marker alleles are located within a region of chromosome 14 between the microscopically visible q11.2 and q32.1 karyotypic bands. The region of chromosome 14 is desirably located between the D14S47 and D14S48 markers, preferably between the D14S52 and D14S55 markers, and most preferably within 20,000–30,000 kb of the D14S43 or D14S53 markers. The locations of these respective markers are indicated in FIG. 1, and exemplary oligonucleotide sequences useful in detecting and isolating each marker are provided below in Table 1. The alleles that make up the genotypes of the genetic markers in the human population (or in a family population) may differ one from the other by as little as a single base pair substitution in the DNA, or the differences may be more substantial involving many base pairs and transversions or transitions. Isolated DNA segments containing the subject genetic marker alleles constitute embodiments of the invention. Two steps are involved in isolating such DNA segments: first, the plurality of alleles of a candidate genetic marker in a family population are isolated (e.g., from genomic DNA); and, second, a candidate marker allele that is indicative of a chromosome 14 Alzheimer's disease trait in the family is selected and isolated as a DNA segment. Illustrative methodology for each of these two steps is next discussed.

A number of different "first steps" will be recognized by skilled artisans as methodological alternatives. For instance, genomic DNA clones having genetic markers may be prepared by microdisection of chromosome 14, i.e., in a region between band q11.2 and band q32.1 (i.e., in Giemsa stained chromosomes). Genomic cloning may then be used to isolate DNA segments having the genetic marker alleles. Alternatively, the genetic markers within the q11.2-q32.1 region of chromosome 14 have nucleotide sequences useful for constructing specific oligonucleotide probes for either fluorescent in situ hybridization or probes in genomic cloning. Illustrative genetic markers from within the q11.2-q32.1 region of chromosome 14 are provided in Table 1, along with corresponding pairs of specific nucleotide sequences that are useful in constructing PCR primers and/or oligonucleotide probes.

Nucleotide sequences specific for the genetic markers in the q11.2-q32.1 region of chromosome 14 are, in turn, useful for detecting clones of cells containing DNA segments with the subject genetic markers. For instance, such oligonucleotide probes may be useful in screening libraries of cloned genomic DNA, flow-sorted chromosome 14 DNA, or radiation-reduced somatic cell hybrid genomic DNA. Isolated DNA segments from the q11.2-q32.1 region (and from subregions therein) are useful, in turn, in common hybridization methods (e.g., Southern blotting) to identify and isolate novel genomic DNA clones that have larger DNA segments or overlapping DNA segments. Such isolated DNA segments may be cloned from primary genomic DNA isolates or from existing genomic DNA libraries. For example, isolated DNA segments may be produced in PCR methods using oligonucleotide primers such as those shown in Table 1, e.g., the primers for D14S43. The isolated DNA segments produced in PCR may be end-labeled with $^{32}p$ and used as probes to screen existing DNA library collections for larger or overlapping isolated DNA segments (e.g., screening cloned λ plasmid libraries, genomic cosmid libraries, or yeast artificial chromosome DNA libraries). In this example, the novel isolated DNA segments prepared in this manner contain at least part of the D14S43 genetic marker, in addition to containing several other novel markers that surround and overlap with the genomic site of D14S43. Sequencing such cloned and isolated genomic DNA segments is useful for identifying different alleles of the markers as they exist in the genomic DNAs of the human population. In addition to isolating DNA segments of overlapping and larger DNA segments, PCR methods are useful for isolating smaller portions of the q11.2-q32.1 region of chromosome 14. Illustrative examples are provided below in Examples 1-3.

A number of "second" steps are useful for detecting and isolating genetic marker alleles that are indicative of a chromosome 14 Alzheimer's disease trait in a family. Each of the genetic markers located within the q11.2-q32.1 region of chromosome 14 has one or more alleles in an individual that constitute the genotype of the marker in that individual. Such alleles may be identified in several ways, including: direct nucleotide sequencing (i.e., of cloned genomic DNA, by processes similar to those described in Example 3), by analysis of genomic DNA fragments (e.g., RFLP fragments, SLTR fragments, fragments of repetitive genomic elements, gene fragments, and the like), or PCR amplified portions of the q11.2-q32.1 region of chromosome 14 (e.g., portions isolated by PCR methods from total genomic DNA; as illustrated in the Examples). Next, the genomic DNA fragments and PCR portions of chromosome 14 that contain indicative genetic marker alleles are selected from among the different alleles of each genetic marker by determining the genetic association between a candidate genetic marker allele and an Alzheimer's trait in a family with a Alzheimer's disease proband. While it may initially be useful to exclude that the disease in the Alzheimer's disease proband is genetically associated with a defect in chromosome 19 or 21, this may not be an absolute requirement because evaluating the genetic association of the candidate genetic marker allele in the family will either indicate such an association, or not. If the result is negative, other candidate genetic marker alleles may be tested, or a chromosome 19 or 21 marker may be tested. For instance, analysis of the pedigree of a candidate genetic marker allele may be sufficient to establish that the candidate allele co-segregates with the Alzheimer's disease trait in the family, or computer-assisted genetic linkage analysis may be helpful to establish such a relationship (e.g., using the LIPED program). In the latter case, an LOD score may be calculated for the association of a candidate genetic marker allele with one or more Alzheimer's disease traits in the family, and the degree of statistical correlation may be calculated as an LOD score at different recombination fractions (RF). A given marker allele exhibits a maximal LOD score at a particular RF. It is desirable that the subject genetic marker alleles that are indicative of a chromosome 14 Alzheimer's disease trait in a family have a maximal LOD score of at least 3 at about RF=0.0 to about RF=0.1; it is preferred that the indicative marker allele have an LOD score of at least 9 at RF=0.0; and it is most preferred that the marker allele have an LOD score of at least 80 at RF=0.0. A candidate genetic marker allele that has the requisite genetic association with the Alzheimer's disease trait in the family is selected as the genetic marker allele indicative of the trait in the family.

The invention provides assays for genetic testing of an individual to determine predisposition of the individual for developing a chromosome 14-linked Alzheimer's disease. The test method requires that the test individual be a member of a family that has a chromosome 14-AD proband (i.e., a clinically affected individual with a chromosome 14 variety of AD). Those skilled in the art will understand that an Alzheimer's disease phenotype may be produced by a chromosome 21, 19, or 14-AD gene, and that genetic testing will be necessary to distinguish among these possibilities and identify a chromosome 14-AD proband. It may be useful in some cases to initiate the subject assay by first conducting genetic testing to exclude individuals clinically affected with a chromosome 21- or chromosome 19-linked Alzheimer's disease. However, the latter exclusionary step is not an absolute requirement of the subject assays because identification of chromosome 14-AD in a clinically affected individual can proceed simulataneously with the determination that the individual is a chromosome 14-AD proband useful in genetic testing of other family members. For example, if the genomic DNA of the patient has a DNA allelic variant of a chromosome 14-AD marker that co-segregates with an Alzheimer's disease phenotype in the pedigree of the family, and if the genome and pedigree of the clinically affected family member also confirm the DNA allelic variant as linked with the AD phenotype in the family, then it can simultaneously be concluded that the clinically affected individual has chromosome 14-AD and is a chromosome 14-AD proband useful in the subject assays. If, on the other hand, the clinically affected family member does not exhibit a DNA allelic variant of a chromosome 14-AD marker segregating with an Alzheimer's disease phenotype in the family, two interpretations are possible: either a) the particular chromosome 14-AD marker is not useful for genetic testing in this particular family, and another chromosome 14-AD marker must be tested; or b) the family member may have a different variety of AD (e.g., a chromosome 19 or 21 linked AD), and this possibility should be tested.

Once an appropriate chromosome 14-AD proband has been identified in a family the next step involves determining the most useful DNA allelic variant(s) of a chromosome 14-AD marker for testing the individuals that make up the members of the family, i.e., the blood relatives and spouses of blood relatives of the clinically affected AD proband. In this step fragments of genomic DNA (e.g., SLTR, RFLP fragments, and the like) are prepared from each of the available members of the family, and each distinctive DNA allelic variant of the polymorphic chromosome 14-AD marker within the family is evaluated to determine which fragment is a DNA allelic variant linked with the Alzheimer's disease phenotype in the family and AD proband. Those skilled in the art will understand that the number of family members evaluated will vary depending upon the pedigrees in different families. It will be necessary to test at least the AD proband and the parents of the proband. It is preferred that the parents of the proband be heterozygous for a DNA allelic variant so that the segregation pattern of the DNA allelic variant linked with an AD phenotype in the chromosome 14-AD proband can be recognized. The DNA allelic variants of chromosome 14-AD markers are conveniently identified by specifically hybridizing a specific oligonucleotide probe (e.g., constructed from one or more of SEQ. ID. NOS. 1–12 in Table 1) with genomic DNA fragments (e.g., RFLPs, SLTRs, and the like) prepared from each of the family members.

Once a DNA allelic variant has been identified that is linked with the AD phenotype in the family, it is only necessary to test any other member of the family for the presence of that particular DNA allelic variant in their genome. If the individual is a genetic member of the family, and has the particular DNA allelic variant in his/her genome, then the individual has a genetic predisposition to develop the disease.

A number of assay formats are useful for such genetic testing. These methods commonly involve nucleic acid binding, e.g., to filters, beads, or microliter plates and the like; and include dot-blot methods, Northern blots, Southern blots, PCR, and RFLP methods, and the like. A variety of natural and synthetic compositions may be used in construction of chromosome 14-AD probes that are specific for the DNA allelic markers linked with an AD phenotype in the family. For example, synthetic oligonucleotide probes, restriction fragments, cDNAs, and the like may be employed. The subject chromosome 14-AD probes are conveniently labeled to allow ease of identification in the subject assays, e.g., by labeling with radionuclides, enzymes, avidin, and the like.

Genomic DNA useful in the subject assays can be conveniently prepared: from blood samples, i.e., obtained from clinically affected family and asymptomatic family members, from continuous lymphoblastoid cell lines established in vitro by Epstein-Bart virus (EBV) transformation of blood samples, or from continuous or primary cultures of other cells, e.g., epithelial, endothelial, or brain cells.

Genotyping to determine DNA allelic variants of a chromosome 14-AD marker in an individual utilizes known methods. Methods for determining marker polymorphism in samples of genomic DNA collected are also known.

Methods for linkage analysis are also understood by those skilled in the art, and several common methods exist for determining whether one marker (e.g., a chromosome 14-AD marker) is linked to another marker (e.g., a marker selected from Table 2 or an AD phenotype). Most commonly in the subject genetic testing assays, linkage is determined by examining segregation patterns in a family pedigree and the recombination of one marker with another known marker already on the chromosome 14 genetic map (i.e., by LOD score at a selected RF as discussed above) within the genomic DNAs of a chromosome 14-AD family.

The subject assays are also useful in combination assays for determining that AD in a family is associated with chromosome 19 or 21, and not with a chromosome 14-AD loci.

Illustrative examples of oligonucleotide probes specific for chromosome 14-AD markers are shown in Table 1. The examples provided in Table 1 include useful DNA sequences for constructing synthetic oligonucleotide PCR primers and oligonucleotide chromosome 14-AD probes. The anonymous DNA clones designated "Mfd" in Table 1 were isolated by Weber et al. (56) by random cloning of short genomic DNA fragments into the m13 vector. Mfd clones contain repetitive SLTR motifs that were selected on the basis of their specific hybridization with poly(dC-dA)-poly(dG-dT). The isolated nucleotide sequences of the Mfd clones were then subsequently determined, and specific sequences were selected for construction of the oligonucleotide probes and primers in Table 1.

TABLE 1

| | Illustrative Ch. 14 AD oligonucleotide probes and PCR primers | | |
|---|---|---|---|
| SEQ. ID. NO. | Locus | cDNA Clone Name[b] | Oligonucleotides |
| (SEQ. ID. NO. 1) | D14S47 | Mfd86 | 5'-CAACATAGCAAGACCCTGTC-3' |
| (SEQ. ID. NO. 2) | | | 5'-GCACATGCCACCAAGACAAG-3' |

TABLE 1-continued

Illustrative Ch. 14 AD oligonucleotide probes and PCR primers

| SEQ. ID. NO. | Locus | cDNA Clone Name[b] | Oligonucleotides |
|---|---|---|---|
| (SEQ. ID. NO. 3) | D14S52 | Mfd167 | 5'-TTACTCCCTGCAAAACAAAC-3' |
| (SEQ. ID. NO. 4) | | | 5'-GATGAATTTCAGAAATGGAG-3' |
| (SEQ. ID. NO. 5) | D14S53 | Mfd190 | 5'-CAACAAGAGCGAAACTCGC-3' |
| (SEQ. ID. NO. 6) | | | 5'-GAAGACTCAAGATATAGCAG-3' |
| (SEQ. ID. NO. 7) | D14S55 | Mfd198 | 5'-AGAACTGTTACCTGGAGGC-3' |
| (SEQ. ID. NO. 8) | | | 5'-AGAGAAGTTAAAAGCATTGC-3' |
| (SEQ. ID. NO. 9) | D14S48 | Mfd48 | 5'-CATAAAAGGCTTATTGGTTTG-3' |
| (SEQ. ID. NO. 10) | | | 5'-CAAAACAGAGAACAGAGTAG-3' |
| (SEQ. ID. NO. 11) | D14S43 | 2E12B | 5'-TGGAACACTCAGGCGA-3' |
| (SEQ. ID. NO. 12) | | | 5'-CCAGAGCCACTTTCTAC-3' | a. Complementary annealing strand primer is listed first for each marker.
[b]Clones isolated and described in citations #56 and #57, except for clone 2E12B (EMBL Accession No. X56973) described in citation #55.

Those skilled in the art will understand that it is routine to construct linkage maps delineating the genomic location (i.e., recombinantion frequency) of a new genetic marker in relation to a known genetic marker. In this manner the markers identified in Table 1 are useful in mapping additional anonymous markers such as the chromosome 14 markers presented below in Table 2. Linkage maps may be rapidly constructed that show the location of many genetic markers within the q11.2–q32.1 region of chromosome 14. For example, in addition to the methods for linkage analysis discussed above, other methods are known by artisans for determining linkage (i.e., of one marker to another). For example, construction of collections genomic DNA of perfect three generation large families (i.e., non-AD families) have been described (e.g., see White, R. et al., 1985, Nature 313: 101–105) and are available from several sources (e.g., "ceph" DNAs available from The American Type Culture Collection and the Camden Institute National Repository). It is also possible to determine the linkage of one marker to another using somatic cell hybridization methods with human-rodent hybrid cells, that contain only a human chromosome 14. In the latter case, the hybrid cells are subjected to DNA-strand breaking levels of radiation followed by cloning to derive radiation-reduced hybrid cell clones, a process referred to as radiation-hybrid mapping (abbreviated RH, below). The relative frequency with which two markers will appear within one clone of radiation-reduced hybrid cells is directly related to the closeness of their linkage within the chromosome 14 genomic DNA, and these frequencies may be used to position and map one marker in relation to another marker within the q11.2–q32.1 region of chromosome 14.

Skilled artisans will recognize that mapping the linkage of 3–5 of the prospective markers (e.g., those in Table 2, below) to the markers in Table 1 (above) should require less than about one week of laboratory analysis. Examples of methods that may be used to determine such linkage are illustrated in Examples 1 and 2 below. Those skilled in the art will also recognize that once a new marker has been placed on the map in the q11.2–q32.1 region of chromosome 14 its utility as a chromosome 14-AD marker may be determined in the subject assays of the invention, as described above, and illustrated below in Examples 1 and 2.

Embodiments of the invention also provide screening methods for identifying novel chromosome 14-linked AD markers. For example, the first step in the method is to construct an oligonucleotide probe specific for a candidate marker that may reside within the q11.2–q32.1 region of chromosome 14 (e.g., a probe such as those for EST00221, EST00201, or EST00008, depicted in Table 2, below). Next, a library of DNA cellular clones is constructed or an existing chromosome 14 library is screened to selected clones with the q11.2–q32.1 region. For instance, genomic chromosome 14 clones are commercially available in a λ vectors. From within this library, a clone with the q11.2–q32.1 region may be selected (e.g., by screening with the oligonucleotide probes and primers in Table 1, above). Once several such q11.2–q32.1 region specific clones have been identified the next step in the subject method is to select among the q11.2q32.1 region specific clones for one clone that has several polymorphic DNA allelic variants identifiable in different members of a chromosome 14-AD family. When such a clone with the requisite DNA allelic variants has been identified the next step is to map the linkage of the DNA allelic variants of the clone to an AD phenotype in a chromosome 14-AD family, (i.e., using the methods described above). The basic method involves selecting a candidate marker (e.g., from Table 2) and analyzing the frequency of that marker in normal chromosomes and AD chromosomes to determine its association with AD, excluding the possibility that any differences observed are due to genetic polymorphism in the marker. Novel chromosome 14-AD markers are identifiable in this manner from within the candidate clones, as markers that map into the q11.2–q32.1 region (i.e., mapped in relation to the markers in Table 1) and desirably having an LOD score for linkage of a candidate DNA allelic variant to an Alzheimer's disease phenotype that is greater than 3 at about RF=0.0 to about RF=0.1; preferably greater than 9 at RF=0.0; and most preferably, greater than 80 at an RF=0.0. Once one novel chromosome 14-AD marker has been identified, it may be added to the list in Table 1 and used to move on and select a second novel marker that may have a still higher linkage with an AD phenotype in a chromosome 14-AD family.

TABLE 2

Chromosome 14 q11.2–q32.1 Markers

| Genetic Marker | Position | Comments (Probe) |
|---|---|---|
| D14S6 | 14 q11–q24.3 | probe p14S3 |
| PYGL | 14 q11–q24.3 | phosphorylase, glycogen storage disease type VI |

TABLE 2-continued

Chromosome 14 q11.2–q32.1 Markers

| Genetic Marker | Position | Comments (Probe) |
|---|---|---|
| D14S2 | 14 q11–q24.3 | probe L1.48 |
| D14S11 | 14 q11–q24.3 | probe pB11.8 |
| ADPRTP2 | 14 q13–q32 | ADP-ribosyltransferase (AND+) pseudogene 2 |
| COX4L1 | 14 q21–qter | Cytochrome C Oxidase subunit IV-like |
| WARS | 14 q21–qter | Tryptophanyl-tRNA Synthetase |
| HSPA2 | 14 q22–q24 | heat shock 70 kd protein 2 |
| ZNF46 | 14 q22–q24 | zinc finger protein 46 (KUP) |
| FRA14B | 14 q23 | fragile site, fra(14)(q23) aphidicolin |
| FRA14C | 14 q24.1 | fragile site, fra(14)(q24.1) |
| ACTN1 | 14 q24.1–q24.2 | actinin, $\alpha_1$ |
| SPTB | 14 q24.1–q24.2 | spectrin, $\beta$ |
| D14S43 | 14 q24.3 | probes 2E12B1/2E12B2/2E12B/ICRFC102E1222 |
| FOS | 14 q24.3 | osteosarcoma oncogene homolog |
| HOX10 | 14 q24.3 | homeobox 10 |
| D14SI2 | 14 q24.3–q32.1 | probe λEMBL3.121 |
| MTHFD | 14 q24 | 5,10-metylene tetra-hydrofolate dehydrogenase, cyclohydrolase and synthetase |
| TGFB3 | 14 q24 | TGF$\beta$3 |
| RNS2 and RNS3 | 14 q24–q31 | ribonuclease 2 and 3 eosinophil-derived neurotoxin and cationic protein |
| D14S32 | 14 | probe CRI-L310 |
| D14S33 | 14 | probe CRI-C15 |
| D14S34 | 14 | probes Mfd42, Mfd42CA/Mfd42GT |
| D14S42 | 14 | probes SJ10F, D14S42 |
| D14S44 | 14 | probe pms627 |
| D14S46E | 14 | probes AS 321, 32B1, DD6, CS1/CS2/CS3/CS4 |
| D14S47 | 14 | probe Mfd86 |
| D14S48 | 14 | probe Mfd101 |
| D14S49 | 14 | probe Mfd119 |
| D14S50 | 14 | probe Mfd130 |
| D14S51 | 14 | probe Mfd165 |
| D14S52 | 14 | probe Mfd167 |
| D14S53 | 14 | probe Mfd190 |
| D14S54 | 14 | probe Mfd192 |
| D14S55 | 14 | probe Mfd198 |
| D14S56 | 14 | probe M146-1/M146-2 |
| D14S57 | 14 | probe MS16-1/MS16-2 |
| D14S58 | 14 | probe MS162-1/MS162-2 |
| D14S59 | 14 | probe MH90-1/MH90-2 |
| D14S60 | 14 | probe pHHH 160 |
| DB1L4 | 14 | diazepam binding inhibitor - like 4 |
| ESAT | 14 | esterase activator |
| FDPSL3 | 14 | farnesyl diphosphate synthetase-like 3 |
| FTHL13 | 14 | ferritin, heavy polypeptide like 13 |
| GALC | 14 | galactosyl ceramidase (Krabe disease) |
| K12T | 14 | K12 temp. sens. comp. |
| LAMRL3 | 14 | laminin receptor-like 3 |
| M195 | 14 | external memb. prot. (195 kd) |
| MSK30 | 14 | antigen for MAb A42 |
| TGM1 | 14 | transglutaminase 1 |
| USH1A | 14 | Usher syndrome 1A |
| VP | 14 | variegate porphyria |
| EST00221 | 14 | brain cDNA and PCR primers: 5'-GTGCCAAGATGGCTCATGTA-3'; (SEQ. ID. NO. 13) 5'-GTATAGCTTTAAGCCAGTTC-3' (SEQ. ID. NO. 14) |
| EST00201 | 14 | brain cDNA and PCR primers: 5'-CCAGGAGAGTAAGAAGATCA-3'; (SEQ. ID. NO. 15) 5'-GCAGAGTTGAATATGAACCT-3' (SEQ. ID. NO. 16) |
| EST00008 | 14 | brain cDNA and PCR primers: 5'-AAGCTGGCTGGGAAATGTTC-3'; (SEQ. ID. NO. 17) 5'-GTCAGTCTAGTAAACTTACAC-3' (SEQ. ID. NO. 18) |

Those skilled in the art will recognize that the nucleotide sequences recited in Table 1 are useful for preparing chromosome 14-AD probes useful in PCR amplification assays illustrated in Example 2 below. The nucleotide sequences of Table 1 are also useful in oligonucleotide probes for screening for DNA clones containing overlapping nucleotide sequence, as well as for primers in chromosome walking and jumping methods to screening for still other genomic DNA clones that contain nucleotide sequences within the q11.2–q32.1 region of chromosome 14, and closely linked with a chromosome 14-AD marker or a chromosome 14-AD phenotype.

Skilled artisans will recognize that the disclosure herein, and compositions and assays that are embodiments of the invention, are useful for identifying genomic DNA clones that have a segment of a q11.2–q32.1 region of chromosome 14 that constitutes a contig with a chromosome 14-AD gene locus. (A detailed illustrative process for isolation of such a conrig is provided in Example 3, below.) Libraries of chromosome 14 DNA are commercially available as FACS flow-sorted chromosome 14 DNA that has been fragmented and cloned into E. coli using a λ vector. Skilled artisans will also recognize that a selected band region (or combination of bands) of chromosome 14 (e.g., band q24.3), may be conveniently scraped from karyotyped DNA, and cloned into a suitable vector, e.g., a cosmid vector (Sambrook, Fritsch, and Maniatis, 1989, *Molecular Cloning, Second Edition*, Cold Springs Harbor Laboratory, 1989, pp. 3.5), λ vector (Sambrook, supra, pp. 2.82), P1 vector (Sambrook, supra, pp. 9.4), or yeast artificial chromosome (YAC; Sambrook, supra, pp. 9.5; described in greater detail below). Artisans will understand that the assays disclosed herein are useful in screening a variety of cloned DNA fragments including human genomic DNA clones, radiation-reduced clones of rodent-human hybrid cells, and the like (as discussed above). Artisans will also understand that methods of screening genomic DNA clones to identify clones that have a particular subregion of a q11.2–q32.1 region of chromosome 14 (e.g., the q24.3 region), are known and that a variety of screening methods may be useful in determining whether an existing clone has such a subregion of chromosome 14. For example, in situ hybridization and cytogenetic analysis is one simple method that may be useful in determining whether the genomic clonal chromosome 14 DNA contains a subregion. Southern blotting may also another simple procedure useful in identifying whether a cloned DNA contains known markers that reside within a particular subregion of the q11.2–q32.1 region of chromosome 14 (e.g., see the markers in FIG. 1; and methods in Sambrook, supra, pp. 9.31). Clones from these libraries may be tested by Southern blot analysis using, for example, a panel of DNA from unrelated human subjects to screen for clones that detect polymorphic sites. Short allele polymorphic loci may be detected in genomic or flow-sorted chromosome 14 libraries by hybridization with synthetic oligonucleotides designed to be complementary to common repeat motifs such as the sequence (CpA). Clones hybridizing to such di-, tri-, and tetranucleotide repeat probes (and longer repeat motifs; such as described in 66) may then be sequenced so that nucleotide sequences for PCR primers may be selected and synthesized. The PCR primers may be used to genotype the respective additional polymorphic loci using conventional methods such as those described in Examples 1–2, below. Single base polymorphic loci may be detected by direct DNA sequencing of cloned DNA from chromosome 14, (e.g., from DNA in a flow-sorted chromosome 14 genomic DNA library). Chromosome 14 gene loci can also be identified by hybridization of genomic clones to members of a cDNA library (67); or, hybridization of cDNA to cloned genomic DNA (70); or, by ligase mediated detection (68); or, by rodent-human somatic cell hybridization methods (69). Polymorphic loci of all types can be assigned to the subject AD region of chromosome 14 (q11.2–q32.1) by genetic mapping as described in the accompanying illustrative Example 2, below.

"YAC" is used to mean a yeast artificial chromosome containing a stretch of human DNA. The YAC exists as one of the chromosomes in a yeast cell and the YAC is reproduced and propagated as a chromosome in the same manner as the natural yeast chromosomes.

"YAC library" is used to mean a collection of YAC clones which cover the entire human genome. All DNA segments which make up the human genome are contained in 1 or more clones of this library. A clone is yeast from a single cell which contains 1 or more YAC's.

The markers in Table 1 (above) may be useful in cloning DNA spanning intervals between 2 markers. This is performed as follows. Primers for a marker (D14S43) are used to screen a YAC library for the corresponding clone. The YAC library is prepared so that it can be screened completely by PCR-based methods without the need for hybridization (105, 106). YAC clones are grown on nylon filters or in 96 well plates and pooled according to the scheme of Amemiya et al. (106). The exact numbers of pools is determined by the redundancy of the library. Likewise, the number of vertical and horizontal pools and corresponding superpools is determined by the number of clones. In this case, 55,000 YAC clones, 5-fold coverage library is divided into 6 "sets", each set consisting of 96 vertical and 96 horizontal pools. The vertical and horizontal pools are combined into 8 superpools each. Screening starts on the superpool level (96 samples). If only 1 superpool is positive, the second screen is 24 samples, which yields the well containing the desired YAC.

Screening of a pool of DNA samples from YAC clones is performed by PCR amplification. The primer set for D14S43 is used to amplifiy a given pool, and the the products analyzed by agarose gel electrophoresis. Positive pools give a band of the appropriate size (approximately 150–190 bp for D14S43). The YAC identified in this manner (105,106) contains the DNA surrounding the initial locus (D14S43) and typically contains up to 2 million bp of DNA from the q11.2–q32.1 region of chromosome 14. The YAC-DNA is then tested for the presence of adjacent markers such as D14S53. This is performed by taking the yeast cell DNA from the appropriate clone and subjecting it to PCR amplifications using the primers for D14S53. If the YAC contains both D14S43 and D14S53, a product will be produced by the D14S53 primers of appropriate size (140–160 bp) as detected by agarose gel electrophoresis. If the YAC does not contain both loci, the ends of the YAC can be cloned by the method of Silverman (107). Once the YAC end is cloned, it can be sequenced, PCR primers prepared, and the YAC library screened as above to identify a second YAC which partially overlaps with the first YAC. This second YAC can then be screened for the presence of D14S53 and D14S43 as described above. This process of sequential screening is termed "chromosome walking" in the art and can be used to clone all of the DNA between 2 markers.

Skilled artisans will recognize that a chromosome 14-AD gene locus may be isolated from within the q11.2–q32.1 region of chromosome 14 in a manner similar to that described in 1983 for the Huntington's disease gene (Gusella et al. 1983) or in 1985 for the cystic fibrosis gene (Tsui et al. 1985; also, references 59–61). A detailed illustrative methodology for such a process is provided below in Example 3.

The chromosome 14-AD gene loci in the q11.2–q32.1 region (or a subregion therein) may for example be one or more of the following: namely, a) trans-regulatory gene loci controlling synthesis of APP (e.g., a locus encoding a polypeptide capable of affecting assembly or degradation of an APP such as a polypeptide protease inhibitor related to the PI/AACT gene family); b) transcriptional regulatory proteins (e.g., related to the c-FOS gene at q24.3); c) chaperon proteins (e.g., related to the heat shock 70 kd HSPA2 gene at position q22–24); or d) some other gene product whose function is presently unkown (as discussed more fully at the end of Example 2, below).

EXAMPLE 1

Description of the Study Population

The families selected for study had three or more affected subjects in two or more generations and at least one case of autopsy-documented AD. Neuropathologic confirmation of AD was obtained for 47 subjects. Families were evaluated either by the University of Washington Alzheimer's Disease Research Center or the University of Minnesota Alzheimer's Disease Research Group. Family LH was independently ascertained at the University of Washington and Duke University. Affected subjects were evaluated, the diagnosis of AD assigned, and autopsies performed as previously described (5,8). Pedigrees for each family have been published elsewhere (1-3,5-8). The SNW family has also been referred to as FAD3 (4) and SW by others (1), and the LH family as family 603 (8,14,17). Table 3 summarizes the characteristics of FAD kindreds used for linkage analysis.

mutations in exons 16 and 17 using both direct sequencing and single-strand conformation variation analysis; no example of the known APP mutations or other variants were observed (18). All family groups were also negative for linkage to more centromeric loci D21S1/S11, D21S13/S16, and D21S215 (8,18).

In addition, the linkage analysis of ENVG pedigrees with chromosome 19 q12–13.3 markers yielded negative LOD scores formally excluding the entire region from D19S13 to KLK. ENVG were tested for linkage of FAD to the following chromosome 19 q12–13.3 markers: D19S13, D19S49, D19S75, D19S47, CYP, ATP1A3, ApoC2, KLK, and D19S180. The resulting LOD scores were uniformly negative and formally excluded the entire region ($Z \leq 2.00$ for $\cong 90$ cM, data not shown) as a location for an early-onset FAD gene.

Thus, for most if not all of the families used in this study, FAD is not caused by mutations at the APP gene, nor by mutations at a more centromeric chromosome 21 locus, or a chromosome 19 locus. After 60

TABLE 3

Characteristics of FAD Kindreds Used for Linkage Analysis

| Family | Total Number Affecteds | Total Number Autopsies | Number Subjects Sampled | Number Affecteds Sampled | Mean age-of-onset ± SD (n) range | Ethnic Origin |
|---|---|---|---|---|---|---|
| Volga German (VG) Kindreds | | | | | | |
| R | 20 | 4 | 29 | 3 | 51 ± 7.1 (17) 40–67 | Volga German |
| W | 4 | 1 | 4 | 2 | 54 ± 3.9 (4) 48–58 | Volga German |
| HD | 23 | 1 | 11 | 6 | 59 ± 10.4 (18) 46–82 | Volga German |
| HB | 21 | 4* | 24 | 4 | 60 ± 7.2 (20) 47–75 | Volga German |
| KS | 12 | 3 | 24 | 6 | 65 ± 5.1 (11) 55–71 | Volga German |
| Early-Onset Non-Volga (ENVG) Kindreds | | | | | | |
| L | 16 | 9* | 23 | 7 | 42 ± 4.6 (16) 30–48 | German |
| AM | 8 | 2 | 10 | 5 | 42 ± 3.2 (8) 36–46 | Japanese |
| HR-XV | 12 | 1 | 7 | 4 | 42 ± 3.9 (6) 37–47 | Hispanic |
| KG | 5 | 2 | 11 | 1 | 44 ± 1.0 (5) 43–45 | British |
| V | 8 | 1 | 9 | 2 | 46 ± 3.8 (7) 41–50 | British (?) |
| HR-I | 13 | 6 | 25 | 3 | 47 ± 4.6 (12) 40–55 | Unknown |
| HR-XIII | 4 | 4 | 11 | 0 | 47 ± 3.6 (4) 41–51 | Unknown |
| LH | 23 | 6 | 27 | 5 | 48 ± 6.5 (18) 37–68 | French-Canadian |
| SNW | 19 | 5 | 17 | 4 | 52 ± 2.5 (7) 48–56 | Russian/Jewish |

*Includes an autopsy on a normal subject;
Includes 1 biopsy

Initially, four groups were defined for separate analysis (8): Volga Germans (VG), early-onset (arbitrarily defined as family mean $\leq 60$ years) non-Volga Germans (ENVG), VG and ENVG combined, and late-onset kindreds. The Volga German families are a group of seven kindreds originating from two villages near the Volga river of Russia (6). FAD in these families is probably the result of a common genetic founder. (VG families E and H were not used because an insufficient number of affected subjects were available for sampling). One ENVG kindred (family 372) was deleted after Goate et al. (9) found that this family had the APP codon 717 Ileu FAD mutation. The role of the APP gene and chromosome 21 in FAD in the remaining ENVG and VG kindreds was evaluated using both linkage and mutational analysis. The families were negative for linkage to the APP gene and to 21 q11 markers, and did not contain mutations in exons 16 and 17 of the APP gene. Linkage to the APP gene was evaluated using a highly informative STRP locus at D21S210 which is closely linked to the APP gene (18). Results of linkage analysis of D21S210 were negative for both groups, and obligate recombinants were observed between the APP gene region and FAD in families AM, HB, HD, HR-I, HR-XV, KS, L, R, and SNW. Affected subjects from each family were also screened for APP markers were typed and analyzed, the late-onset families were dropped from the study in order to reduce the number of samples that needed to be genotyped and the computer time required for analysis. An additional 4 markers were typed on the VG and ENVG families. Of a total of 64 markers, 14 were on chromosome21, with most clustered at 21q11.1–21.1, and 17 were on chromosome 19 clustered at position q12–13.3. The remaining 33 markers were on other autosomes.

EXAMPLE 2

Genetic Markers, Statistical Models, and Analyses

Markers were screened for linkage to FAD by the LOD score method (24) under two models. In the first model, age-dependent penetrance was assumed using the family-specific age-of-onset mean and a standard deviation of 11.99 derived from the original group of families (VG, ENVG and late-onset families). For the second model, penetrance was set at 1% such that no assumptions about the age-dependence of FAD onset were made. For both conditions, LOD scores were computed at FAD gene frequencies of 0.001, 0.01, and 0.06. These six conditions were routinely used to test the robustness of the exclusion and inclusion results. During screening of the genome, the initial two sites chosen for chromosome 14 were D14S1 and the a 1- antitrypsin/α₁-antichymotrypsin gene cluster (PI-/AACT). D14S1 was selected because of its proximity to Gm (immunoglobulin heavy chain gene cluster), which was reported to give positive LOD scores for linkage to FAD in one family (2). PI/AACT were chosen because AACT is a candidate gene for AD (38). Both gave significant negative LOD scores at close recombination fractions (Table 4) and appeared to exclude both AACT and PI as being FAD loci. Since each locus gave small nonsignificant positive LOD scores at more distant recombination fractions for the ENVG group, two additional short tandem repeat polymorphic (STRP) markers, D14S43 and TCRD, were selected to test whether the positive LOD scores with PI/AACT were the result of a more centromeric FAD locus (FIG. 1).

When D14S43 was analyzed using the standard screening conditions, strong positive LOD scores for ENVG families were obtained for all recombination fractions for both the age-corrected penetrance and the affected only (1% penetrance) models (Table 4). Significant results ($Z_{max}>3.00$) were obtained for both models with all FAD gene frequencies tested. The computational parameters used for screening were chosen to give conservative LOD score estimations (Table 4) for all family groups (ENVG, VG, and late-onset). Genotype analysis was performed as previously described (33,39, see the appended Materials and Methods). Briefly, synthetic oligonucleotides were prepared to different STRP chromosome 14 marker loci described and sequenced by Wang et al. (56) and to the D14S43 marker described and sequenced by Sharma et al. (55). The synthetic oligonucleotides were used as PCR primers, in standard PCR methods, to amplify the respective chromosome 14 regions (indicated in Table 4) from genomic DNA of EBV-transformed lymphoblastoid cell lines prepared from each of the different AD kindred. The genotype of each PCR amplified sample was scored for allele size compared to molecular size standards. For D14S43, genotype determinations were repeated for all family subjects with a final error rate of less than 1%. LOD scores were calculated using a cumulative normal age-of-onset correction (8, see below). Family-specific age-of-onset means were used with a standard deviation of 11.99 years derived from the overall group (ENVG+VG+late-onset) for markers AACT, D14S1, D14S43, PI, and TCRD, or standard deviation of 9.52 years derived from the VG+ENVG group for the remaining loci. LOD scores in parenthesis were calculated under the assumption of 1% penetrance. All values were computed using a FAD gene frequency of 0.001.

TABLE 4

LOD scores for Linkage of FAD to Chromosome 14 Loci

| Marker | PIC* | Family Group | \multicolumn{7}{c}{Recombination Fraction (Θ)} | | | | | | |
|---|---|---|---|---|---|---|---|---|---|
| | | | 0.001 | 0.05 | 0.10 | 0.15 | 0.20 | 0.30 | 0.40 |
| TCRD | 0.74 | ENVG | −10.34 | −4.52 | −2.84 | −1.86 | −1.21 | −0.44 | −0.09 |
| | | VG | −8.44 | −3.63 | −2.28 | −1.50 | −0.99 | −0.38 | −0.09 |
| D14S47 | 0.58 | ENVG | −5.29 | −0.87 | −0.01 | 0.35 | 0.48 | 0.39 | 0.15 |
| | | VG | −6.25 | −2.76 | −1.80 | −1.22 | −0.82 | −0.34 | −0.10 |
| D14S52 | 0.58 | ENVG | 2.02 | 4.59 | 4.56 | 4.19 | 3.64 | 2.25 | 0.08 |
| | | VG | −4.60 | −1.26 | −0.52 | −0.17 | 0.01 | 0.08 | 0.01 |
| D14S43 | 0.72 | ENVG | 8.91 | 8.40 | 7.67 | 6.79 | 5.79 | 3.55 | 1.33 |
| | | VG | −6.41 | −1.51 | −0.47 | −0.02 | 0.16 | 0.16 | 0.03 |
| D14S53 | 0.68 | ENVG | 4.24 | 7.12 | 6.88 | 6.19 | 5.28 | 3.10 | 0.99 |
| | | VG | −3.58 | −2.49 | −1.74 | −1.21 | −0.82 | −0.30 | −0.06 |
| D14S55 | 0.51 | ENVG | −1.32 | 0.43 | 0.66 | 0.70 | 0.64 | 0.43 | 0.19 |
| | | VG | −6.97 | −3.12 | −1.51 | −0.69 | −0.27 | 0.00 | −0.05 |
| D14S48 | 0.73 | ENVG | −10.96 | −2.56 | −0.93 | −0.15 | 0.25 | 0.41 | 0.13 |
| | | VG | nd | nd | nd | nd | nd | nd | nd |
| AACT | | ENVG | −2.35 | 0.06 | −0.52 | 0.68 | 0.69 | 0.46 | 0.16 |
| | | VG | −3.58 | −1.77 | −1.22 | −0.86 | −0.60 | −0.25 | −0.06 |
| PI | 0.89 | ENVG | −9.72 | −2.52 | −0.69 | 0.16 | 0.55 | 0.61 | 0.24 |
| | | VG | −9.08 | −3.43 | −2.01 | −1.29 | −0.87 | −0.43 | −0.18 |
| D14S51 | 0.79 | ENVG | −17.70 | −5.10 | 02.08 | −0.59 | 0.20 | 0.69 | 0.47 |
| | | VG | −13.33 | −6.38 | −3.76 | −2.27 | −1.37 | −0.44 | −0.11 |

*PIC is polymorphic information content;
"nd" indicates not determined.

Once linkage to D14S43 was detected, parameters for additional calculations were selected which are more appropriate for the ENVG and VG groups. In particular, a FAD gene frequency of 0.001 was used since early-onset FAD is rare. Also, group-specific age-of-onset standard deviations were used in the age-corrected analysis (Table 5). The standard deviation did not significantly affect the results (as indicated by comparing the results for D14S43 in Tables 4 and 5). Under these conditions, the maximum LOD scores for linkage of D14S43 to FAD in the ENVG group was 9.15 (Θ=0.01) for the age-corrected penetrance model and 5.94 (Θ=0.0) for the 1% penetrance model. Much of the positive evidence for linkage came from families L ($Z_{max}$=4.89, Θ=0.00) and SNW ($Z_{max}$=2.17, Θ=0.0). Of the 9 ENVG families, 6 gave positive LOD scores at all recombination fractions, 1 (AM) was uninformative, 1 (HR-XV) gave negative LOD scores with the age-corrected analysis and positive scores under the 1% penetrance model, and 1 family (V) was negative for both models (Table 5). Family and group LOD scores for linkage of FAD to D14S43 were calculated as described above in relation to Table 4; using group-specific standard deviations of 5.60 years for the ENVG families and 8.62 years for the VG group.

TABLE 5

| Family Group | Family | \multicolumn{7}{c}{Recombination Fraction (Θ)} | | | | | | | $Z_{max}(\Theta)$ |
|---|---|---|---|---|---|---|---|---|---|
| | | 0.00 | 0.05 | 0.10 | 0.15 | 0.20 | 0.30 | 0.40 | |
| VG | HB | −5.58 | −2.29 | −1.38 | −0.88 | −0.57 | −0.23 | −0.08 | |
| | | (−0.81) | (0.21) | (0.30) | (0.29) | (0.23) | (0.10) | (0.00) | 0.31 (0.11) |

TABLE 5-continued

| Family Group | Family | Recombination Fraction (Θ) | | | | | | | $Z_{max}(\Theta)$ |
|---|---|---|---|---|---|---|---|---|---|
| | | 0.00 | 0.05 | 0.10 | 0.15 | 0.20 | 0.30 | 0.40 | |
| | HD | −1.65 | 0.09 | 0.20 | 0.19 | 0.13 | −0.03 | −0.09 | 0.20 (0.10) |
| | | (−1.63) | (−0.32) | (−0.15) | (−0.09) | (−0.06) | (−0.04) | (−0.03) | |
| | KS | −2.26 | 0.00 | 0.19 | 0.26 | 0.26 | 0.20 | 0.10 | 0.26 (0.15) |
| | | (−1.01) | (−0.10) | (0.05) | (0.10) | (0.11) | (0.09) | (0.05) | 0.11 (0.20) |
| | R | 0.15 | 0.10 | 0.05 | 0.01 | −0.02 | −0.03 | −0.01 | 0.15 (0.0) |
| | | (0.17) | (0.11) | (0.06) | (0.03) | (0.01) | (0.0) | (0.0) | 0.17 (0.0) |
| | W | −0.98 | −0.54 | −0.35 | −0.24 | −0.16 | −0.06 | −0.01 | |
| | | (0.29) | (0.25) | (0.21) | (0.17) | (0.13) | (0.06) | (0.02) | 0.29 (0.001) |
| | VG Total | −10.32 | −2.65 | −1.28 | −0.65 | −0.35 | −0.15 | −0.10 | |
| | | (−2.99) | (0.14) | (0.48) | (0.50) | (0.42) | (0.20) | (0.04) | 0.50 (0.15) |
| ENVG | AM | 0.00 | 0.01 | 0.02 | 0.02 | 0.02 | 0.01 | 0.00 | 0.02 (0.06) |
| | | (0.21) | (0.16) | (0.13) | (0.10) | (0.07) | (0.03) | (0.01) | 0.21 (0.0) |
| | HR-I | 1.44 | 1.23 | 1.04 | 0.86 | 0.68 | 0.35 | 0.08 | 1.44 (0.0) |
| | | (0.71) | (0.53) | (0.40) | (0.30) | (0.22) | (0.08) | (−0.02) | 0.71 (0.0) |
| | HR-XIII | 0.30 | 0.26 | 0.22 | 0.19 | 0.14 | 0.07 | 0.02 | 0.30 (0.0) |
| | | (0.09) | (0.07) | (0.05) | (0.04) | (0.02) | (0.01) | (0.00) | 0.09 (0.0) |
| | HR-XV | −0.91 | −0.40 | −0.22 | −0.13 | −0.07 | −0.02 | 0.00 | |
| | | (0.48) | (0.43) | (0.37) | (0.31) | (0.25) | (0.13) | (0.04) | 0.48 (0.0) |
| | KG | 0.88 | 0.84 | 0.77 | 0.69 | 0.59 | 0.36 | 0.13 | 0.88 (0.0) |
| | | (0.48) | (0.42) | (0.36) | (0.30) | (0.24) | (0.12) | (0.03) | 0.48 (0.0) |
| | L | 4.89 | 4.47 | 4.03 | 3.57 | 3.09 | 2.03 | 0.89 | 4.89 (0.0) |
| | | (2.49) | (2.25) | (2.01) | (1.75) | (1.48) | (0.93) | (0.36) | 2.49 (0.0) |
| | LH | 1.31 | 1.23 | 1.11 | 0.96 | 0.79 | 0.45 | 0.16 | 1.31 (0.0) |
| | | (1.29) | (1.15) | (0.99) | (0.83) | (0.66) | (0.35) | (0.12) | 1.29 (0.0) |
| | SNW | 2.17 | 2.02 | 1.81 | 1.56 | 1.29 | 0.71 | 0.22 | 2.17 (0.0) |
| | | (0.61) | (0.59) | (0.52) | (0.42) | (0.31) | (0.11) | (0.01) | 0.61 (0.0) |
| | V | −0.99 | −0.75 | −0.56 | −.040 | −0.28 | −0.11 | −0.02 | |
| | | (−0.42) | (−0.17) | (−0.04) | (0.03) | (0.07) | (0.08) | (0.06) | 0.08 (0.30) |
| | Total (ENVG) | 9.09 | 8.92 | 8.23 | 7.32 | 6.25 | 3.86 | 1.47 | 9.15 (0.01) |
| | | (5.94) | (5.44) | (4.78) | (4.07) | (3.33) | (1.84) | (0.61) | 5.94 (0.0) |
| | Total (VG + ENVG) | −1.23 | 6.27 | 6.95 | 6.66 | 5.91 | 3.71 | 1.37 | 6.95 (0.10) |
| | | (2.96) | (5.58) | (5.26) | (4.57) | (3.75) | (2.04) | (0.65) | |

The VG kindreds gave negative LOD scores at all recombination fractions when the age-corrected penetrance function was used, but yielded small nonsignificant positive LOD scores under the 1% penetrance model ($Z_{max}=0.50$, $\Theta=0.15$; Table 5). When a between-group heterogeneity test (see below) was used to compare the ENVG to the VG group, statistically significant evidence for heterogeneity ($\chi^2=1.833$, p=0.014) was obtained when the age-dependent model was used but not when the 1% penetrance model was used. There was no evidence for heterogeneity within the ENVG or the VG group. However, the lack of statistical evidence for heterogeneity does not exclude the possibility that some of the ENVG families may not map to chromosome 14.

Additional STRP loci were then tested to localize the chromosome 14 AD locus (FIG. 1). The CEPH family panel was used to place D14S43 on a recently described STRP chromosome 14 map (39)(FIG. 1). Flanking markers D14S52 and D14S53 gave significant positive LOD scores of $Z_{max}=4.64$ ($\Theta=0.07$) and $Z_{max}=7.12$ ($\Theta=0.05$), respectively. The AM family, which was uninformative for D14S43, gave suggestive positive LOD scores with D14S53 ($Z_{max}=1.44$, $\Theta=0.001$, and $Z_{max}=1.19$, $\Theta=0.001$, for age-corrected and 1% penetrance models, respectively). Markers D14S47, D14S55, and D14S48 gave negative values for close linkage and small positive but nonsignificant values at larger recombination fractions.

These data provide strong evidence for an early-onset FAD locus at 14 q24.3. The LOD scores substantially exceed 3.00, the threshold value for statistical significance. When the original screening $Z_{max}$ of 8.91 is corrected for multiple models tested, a conservative LOD score of $Z_{max}=8.12$ is obtained for age-corrected analysis. This value corresponds to a probability of linkage exceeding 99.99% (see below). Highly significant LOD scores were also obtained using the 1% penetrance model despite the loss of power to detect linkage under this model.

Thus, the evidence for linkage is not dependent on the assumptions used to correct for age-dependent penetrance. Families to be tested should first be checked by mutational and linkage analysis to exclude the possibility that mutations in the APP are responsible for the disease in a given family. In addition, it may be necessary to exclude families showing strong evidence for linkage to chromosome 21 q11 and/or chromosome 19 q1213.3 markers. In the present studies, the data showing the lack of linkage of AD in ENVG families with chromosome 19 markers is presented in Table 6.

TABLE 6

LOD Scores for Linkage of FAD to Chromosome 19 Loci in Early-Onset Non-Volga Germa Families.

| Marker | 0.001 | 0.05 | 0.10 | 0.15 | 0.20 | 0.30 | 0.40 |
|---|---|---|---|---|---|---|---|
| Na/K ATPase | −16.61 | −7.69 | −4.91 | −3.27 | −2.18 | −0.87 | −0.24 |
| | (−9.99) | (−5.15) | (−3.18) | (−2.08) | (−1.40) | (−.061) | (−.021) |
| D19S13 | −7.37 | −3.16 | −2.04 | −1.39 | −0.95 | −0.37 | −0.07 |
| | (−4.55) | (−2.49) | (−1.58) | (−1.04) | (−0.69) | (−0.29) | (−0.08) |
| CYP-2 | −14.94 | −5.79 | −3.65 | −2.55 | −1.72 | −0.68 | −0.16 |
| | (−4.06) | (−1.67) | (−0.78) | (−0.34) | (−0.11) | (0.05) | (0.05) |
| BCL | −9.83 | −4.61 | −3.16 | −2.28 | −1.64 | −0.70 | −0.16 |

TABLE 6-continued

LOD Scores for Linkage of FAD to Chromosome 19
Loci in Early-Onset Non-Volga Germa Families.

| Marker | 0.001 | 0.05 | 0.10 | 0.15 | 0.20 | 0.30 | 0.40 |
|---|---|---|---|---|---|---|---|
|  | (−4.87) | (−2.78) | (−1.64) | (−0.96) | (−0.54) | (−0.14) | (−0.02) |
| D19S11 | 0.14 | 0.26 | 0.31 | 0.32 | 0.29 | 0.19 | 0.07 |
|  | (0.30) | (0.27) | (0.24) | (0.20) | (0.16) | (0.08) | (0.02) |
| ApoCII | −16.31 | −6.67 | −4.17 | −2.68 | −1.67 | −0.48 | 0.00 |
|  | (−8.32) | (−4.20) | (−2.76) | (−1.47) | (−0.85) | (−0.21) | (0.01) |
| D19S47 | −16.69 | −6.00 | −3.67 | −2.40 | −1.58 | −0.63 | −0.18 |
|  | (−10.52) | (−4.71) | (−3.03) | (−2.17) | (−1.43) | (−0.65) | (−0.22) |
| KLK | −9.50 | −3.87 | −2.40 | −1.58 | −1.03 | −0.37 | −0.06 |
|  | (−0.34) | (−0.37) | (−0.27) | (−0.17) | (−0.08) | (0.00) | (0.00) |
| CEA | −14.88 | −6.58 | −4.31 | −2.94 | −2.01 | −0.85 | −0.25 |
|  | (−5.15) | (−2.23) | (−1.42) | (−0.94) | (−0.63) | (−0.28) | (−0.25) |
| D19S75 | −13.19 | −5.76 | −3.70 | −2.49 | −1.66 | −0.66 | −0.16 |
|  | (−5.87) | (−2.10) | (−1.17) | (−0.67) | (−0.38) | (−0.09) | (0.00) |
| D19S49 | −15.12 | −5.10 | −2.67 | −1.39 | −0.64 | 0.04 | 0.12 |
|  | (−6.95) | (−2.62) | (−1.27) | (−0.59) | (−0.23) | (0.03) | (0.03) |
| D19S180 | −31.58 | −13.11 | −8.34 | −5.57 | −3.73 | −1.55 | −0.51 |
|  | (−15.75) | (−7.31) | (−4.52) | (−2.92) | (−1.90) | (−0.75) | (−0.25) |

FAD gene frequency 0.001; computed using age-dependent penetrance function;
values in parenthesis were computed using a 1% penetrance model;
chromosome 19 map: D19S11, 65 cm; D19S13, 83.7 cm; D19S49, 84.9 cm; D19S75, 88.7 cm; D19S47, 101.1 cm; CYP, 105.2 cm; ATP1A3, 108.2 cm; BCL3, 112.9 cm; ApoC2, 115.7 cm; KLK, 134.1 cm; and D19S180, 144.4 cm.

The negative results for the Volga German families could indicate that an additional locus exists on some chromosome other than 14 or 21. An alternative interpretation is that the penetrance model used for the VG families is incorrect and that a chromosome 4 locus contributes to the disease in the VG families.

These results have several implications for both the genetics of FAD and the pathogenetic mechanisms responsible for disease. First, this work confirms the hypothesis that FAD is genetically heterogeneous (30,31); early-onset FAD can be caused by mutations either at the APP gene or at an as yet unidentified chromosome 4 locus. In addition, other FAD loci may exist at other locations. Second, these results demonstrate that FAD, a complex genetically heterogeneous disease, can be successfully approached using a combination of linkage analysis and molecular genetic techniques. Future work will include determining whether the chromosome 14-AD gene locus is responsible for some or all late-onset FAD. Unraveling the genetics of FAD will ultimately contribute to resolving the role of inheritance in apparently "sporadic" AD, the most common form of the disease. Third, the eventual identification of the chromosome 14-AD gene should help resolve the pathogenic mechanism(s) responsible for AD. For example, the chromosome 14 gene locus may be involved in APP processing. Several potential chromosome 14 candidate genes for this role include the protease inhibitors encoded by the AACT and PI genes and the protease cathepsin G at band 14 q11. However, these loci do not appear to be located in the correct region, and the PI/AACT cluster appears to be excluded by the linkage data (Table 4). Other potential candidate loci which map to the 14 q24 region include the c-FOS gene at band q24.3 and the heat shock 70 kd protein (HSPA2) at band q22-q24 (42). The c-FOS protein, when complexed with c-Jun, acts as a transcription factor which binds to AP-1 sites such as those found in the promoter of the APP gene (43); thus c-FOS may be involved in transcriptional regulation of the APP gene. The HSPA2 gene product is a molecular chaperon potentially involved in protein assembly and degradation (48) and thus could act in one of the APP processing pathways. In addition, the gene products from both c-FOS and HSPA2 have been implicated in injury response mechanisms in the central nervous system (47,48). The possibility also exists that the chromosome 14-AD gene locus defines a pathogenetic mechanism which is completely distinct from APP processing. In any event, the results of this study open an important new line of research; identification of the chromosome 14-AD gene locus will play a critical role in resolving the pathogenesis of AD.

MATERIALS AND METHODS FOR EXAMPLES 1 AND EXAMPLE 2

PCR Genotyping Assay:

For genotype analysis, PCR (polymerase chain reaction) was used to amplify polymorphic regions containing STRP sequences (64). The basic amplification procedure was to mix subject DNA (200–1000 ng) with 70 µM of each dNTP, approximately 10 pmol of each primer, 10 mM Tris-HCl (pH 8.4), 50 mM KCl, 0.001% gelatin, 1.0–3.0 mM $MgCl_2$, and 1–3 units Taq polymerase (Perkin-Elmer) in a final volume of 10–100 µl. Thermocycling conditions were 30 sec at 94° C., 30 sec at 60° C., and 45 sec at 72° C. with 5 sec added to the 72° C. step up each of 30 cycles, using a Thermal Cycler 9600 thermocycler (Perkin-Elmer) (conditions used were essentially as described in 64;65). Amplification conditions varied from this basic procedure depending on the primer pair and the sequence to be amplified. Routinely, one of the 2 primers was end-labeled with $^{32}P$ using $\gamma^{32}P$-ATP and kinase. (Sequencing gels and kinase $^{32}P$ end-labeling reaction were performed according to Maniatis et al., supra). For some marker loci, unlabeled primers were used and radiolabeled nucleotides were included in the amplification mixture. After amplification, the samples were subjected to electrophoresis using a polyacrylamide DNA sequencing gel to resolve different alleles. Molecular size standards used were either DNA sequencing ladders or human samples with alleles of known size. After electrophoresis, the gels were dried down and autoradiography was used to visualize the pattern of the alleles and size markers.

The PI gene was genotyped by amplifying 3 portions of the gene followed by digestion with restriction enzymes. Primer sequences were taken from the published PI gene sequence (51), GenBank accession number K02212, and were numbered accordingly. PI40471

(SEQ. ID. NO. 14)(AGTGAAGTCATTTACC-CCAGG) and PI4047R (SEQ. ID. NO. 20) (GGTTCATTATGCCTCCCAAGC) produce a 466 bp product beginning at base 2096 which contains 2 bi-allelic restriction fragment length polymorphism (RFLP) sites detected by digestion with MspI and AvaII (52). PI75951 (SEQ. ID. NO. 21) (GCTGACACTCACGATGAAATCC) and P 17595r (SEQ. ID. NO. 22) (ACTTATCCACTAGCTT-CAGGC) produce a 181 bp product starting at base 5644 which contains a bi-allelic RFLP at codon 101 detected by digestion with RsaI (53). PI93501 (SEQ. ID. NO. 23)(TCTGCTACACTCTTCCAAACC) and PI9350r (SEQ. ID. NO. 24) (GGTGAGTTCATT-TACCAGGTGC) produces a 292 bp product beginning at base 7399 which contains an RFLP site at the codon for Val213 which can be detected by digestion with BstEII (54). For genotyping, the 5644 and 7399 fragments were amplified and digested together. Restriction digest bands were resolved by nondenaturing polyacrylamide gel electrophoresis and detected by staining with ethidium bromide. The 2096 fragment was amplified alone, double digested with MspI and AvaII, and the bands resolved and detected in the same manner. Since both polymorphic sites were on the same fragment, in most cases haplotypes could be determined directly from the double digest band pattern. However, when a subject was homozygous for the presence of the AvaII site and heterozygous for the MspI site, a second digest with MspI alone was needed to determine the haplotype unambiguously. D14S1 and AACT genotypes were determined by Southern blotting techniques. For AACT, a partial cDNA clone was used to identify the following polymorphic sites: a TaqI bi-allelic RFLP with band sizes of 2.8 and 5.8 kb and allele frequencies of 0.3 and 0.7, respectively; a bi-allelic StuI RFLP system with bands of 17.5 kb and 7.0 and frequencies of 0.64 and 0.36, respectively; a StuI polymorphic site with allelic bands of 1.1 kb and 0.95 kb with frequencies of 0.12 and 0.88, respectively; and a bi-allelic ApaI RFLP with 2.1 kb and 1.65 kb alleles with frequencies of 0.11 and 0.89, respectively.

For the STRP loci D14S43, D14S47, D14S48, D14S52, D14S53, D14S55, and TCRD, the primers and amplification conditions used were those described by others (39,55).

LOD scores were calculated using the computer program LIPED modified to handle up to 20 alleles and the capacity to handle different alleles for each family. LOD scores were calculated assuming autosomal dominant inheritance using either a cumulative normal age-dependent penetrance function and an FAD gene frequency of 0.001 or a fixed value of 1% penetrance with no age-dependence. Possible heterogeneity between the two groups of families was examined using the M test (37) and the A test (36). The M test was used to test for heterogeneity within each of the two family groups.

The posterior probability of linkage given a maximum LOD score of L was approximated using the following equation (40):

$$P(H_1/D) = 0.02R/(0.02R + 0.98,\qquad 5.$$

where $H_1$ is the alternative hypothesis of linkage, D is the observed data, and R is the critical odds ratio, or $10^L$. With equation 1 (see above), a LOD score of 3.0 with an odds ratio of 1000:1 corresponds to a posterior probability of linkage of approximately 95%, while an LOD score of 6 with an odds ratio of 1,000,000:1 corresponds to a posterior probability of linkage of 99.995%, and a LOD score of 8 corresponds to a posterior probability of linkage of 99.99995%. To correct for the use of multiple models and to avoid an inflated type I error potentially caused by maximizing the LOD score over models, the maximum LOD score of 8.91 was reduced by the conservative correction of 0.78=log 6 to account for the 6 models used (3 gene frequencies, 2 penetrance functions). If, in addition, a correction is made for the 64 markers typed in the genome search, the maximum LOD score is reduced by an additional 1.81=log 64, bringing the maximum value down to 6.32, which is still highly significant. Note that for the moderate number of independent markers tested in this study, arguments by Ott (40) and Risch (41) indicate that the adjustment of the maximum LOD score for this number of markers is probably not necessary.

For all STRP markers, allele frequencies used were those published, combined with data for an additional 100 Caucasians. For D14S43, D14S52, and D14S53, allele frequencies used for the AM family were from 90 Japanese subjects. For D14S43, allele sizes and combined Caucasian frequencies are: 193 bp, 0.007; 191 bp, 0.007; 189 bp, 0.067; 187 bp, 0.135; 185 bp, 0.151; 183 bp, 0.130; 181 bp, 0.044; 179 bp, 0.017; 177 bp, 0; 175 bp, 0.003; 171 bp, 0; 169 bp, 0.003; 163 bp, 0.003; 161 bp, 0.014; 159 bp, 0.418; and 155 bp, 0.003, respectively. The D14S43 Japanese allele frequencies were 0.0, 0.0, 0.006, 0.150, 0.083, 0.411, 0.094, 0.017, 0.006, 0.006, 0.011, 0.006, 0.0, 0.0, 0.211, and 0.0, respectively.

A table of LOD scores for linkage of chromosome 19 markers to FAD in the current families demonstrates that the early-onset families do not map to chromosome 19, a region indicated by other work to be the potential location of a late-onset locus.

EXAMPLE 3

Summary Overview:

The steps (detailed below) that lead to cloning of the chromosome 14-AD gene locus (loci) may be summarized as follows:

Step 1) Genetic Mapping Techniques

Purpose: The purpose of genetic mapping techniques is to identify the map location of the AD locus to within 1-2 cM within subregions of the q11.2-q32.1 region of chromosome 14.

The location of the chromosome 14-AD gene locus (loci) is refined to as small a subregion of the q11.2-q32.1 region of chromosome 14 as possible using genetic mapping techniques (e.g., 2-point and multipoint linkage analysis and linkage disequilibrium methods such as those described above in Examples 1-2). The subregion of interest is localized to within 1-2 cM. Fine mapping of the AD gene locus involves constructing high resolution genetic maps of subregions of the q11.2-q32.1 region of chromosome 14. The preferred markers for use in the fine mapping are those that are highly informative, i.e., with polymorphic information content (PIC)>0.6. The ordering of polymorphic markers on the fine structure map is achieved by both genetic mapping techniques and also by mapping the order and relative distance between the markers in radiation-reduced somatic cell hybrids (RH mapping) and by localizing markers within chromosomal band regions using fluorescence in situ hybridization methods.

Step 2) YAC and Cosmid Cloning

Purpose: The purpose of YAC and cosmid cloning is to isolate clones containing the isolated DNA segments of subregions of chromosome 14 that contain the genetic markers that are closely linked with AD gene locus (loci).

The chromosome 14-AD gene locus (loci) is most conveniently cloned using yeast artificial chromosome vectors (YACs) and cosmid genomic DNA cloning vectors. YACs containing the q11.2–q32.1 region of chromosome 14 are identified using probes and PCR primer sets from genes, STRP loci, CpG islands, and sequence tagged sites (STS's) which are specific for nucleotide sequences selected from markers that have been placed on the radiation-hybrid maps (above) and genetic maps (above) of subregions of q11.2–q32.1. In addition, pulse-field gel electrophoresis (PFGE) mapping is useful in determining the relative physical distances between markers as well as any possible gaps that may exist between markers that may require additional cloning of overlapping segments in YACs or cosmid clones.

Step 3) Identification of Candidate Genes

Purpose: The purpose of this step is to identify candidate genes within the subregions of the q11.2–q32.1 region of chromosome 14.

Candidate genes in the q11.2–q32.1 region and its constituent subregions are identified by nucleotide sequencing of isolated DNA segments in the YAC clones and cosmid clones (described above in Step 2). The methodologies useful in this step are detailed below.

Step 4) Identification of the Chromosome 14-AD Gene Locus (Loci)

Purpose: The purpose of this step is to identify the AD gene locus (loci) from within the candidate genes identified in Step 3 (above).

The nucleotide sequences obtained above (Step 3) from clones containing isolated DNA segments from the various constituent subregions of the q11.2–q32.1 region of chromosome 14 is useful in identifying specific nucleotide insertions and/or deletions (e.g., by Southern blotting) that correlate with the presence of an Alzheimer's disease trait. Point mutations or small insertions or deletions that may exist in subregions of the q11.2–q32.1 region of chromosome 14 are identified by nucleotide sequencing of cosmid or YAC clones containing segments of genomic DNA from members of chromosome 14-AD families, or the cloned DNA segments may be subjected to single-strand sequence analysis (SSCA) to identify a mutation that co-segregates with the chromosome 14-AD trait (or phenotype) in the family.

I. Step 1) Genetic Mapping Techniques:

A. Multipoint Linkage Analysis:

Multipoint linkage analysis is performed for detailed mapping of subregions of the q11.2–q32.1 region of chromosome 14 that contain the AD gene locus (loci). Multipoint analysis serves to localize the most likely region containing an AD locus within the confines of the chromosome 14 q11.2–q32.1 map (FIG. 1). As additional genetic markers within subregions of q11.2–q32.1 are identified, additional multipoint analyses confine a chromosome 14-AD gene locus to within successively smaller subregions of the q11.2–q32.1 genomic map. ENVG families (i.e., such as those described in Examples 1 and 2, above) are particularly useful in these analyses since complications posed by genetic heterogeneity (i.e., when estimating a chromosome 14-AD gene locus map position) are best addressed by using a complete set of family results to estimate (jointly) the genetic location and the heterogeneity parameter (for further explanation see below).

Multipoint analyses are conveniently performed using the LINKAGE package of computer programs, which uses a "full likelihood" approach to linkage analysis and therefore can handle large amounts of data that is commonly missing in such family studies. The multipoint analyses consist primarily of 3-point analyses (i.e., 2 markers plus the AD trait or AD phenotype).

B. Generic Heterogeneity:

Given that the chromosome 14-AD is genetically heterogeneous (Examples 1–2, above), it is necessary to jointly estimate the fraction of linked families and the recombination fraction in these families to avoid a bias or inconsistent estimate of the map position of a chromosome 14 AD gene locus. As new ENVG families are added to the analyses it is necessary to eliminate families in which the Alzheimer's disease is not a chromosome 14-AD, and is instead the result of an APP mutation (i.e., in chromosome 19 or 21). Possible linkage of the Alzheimer's disease in a new ENVG family to the APP gene is conveniently tested using the STRP locus D21S10 genetic marker, and in addition exons 16 and 17 of the APP gene may be sequenced from at least one of affected member of each family. Any new ENVG family that show a significant positive LOD score for linkage to APP (i.e., $Z_{max} > \text{or} = 3.0$) or having one or more mutations in exon 16 or 17 of the APP gene is excluded from the analyses. All other qualifying families are used in the multipoint linkage analysis of chromosome 14 genetic markers, e.g., using the HOMOG computer program and the data resulting from simultaneous analysis of the alleles of at least 3–5 genetic markers (i.e., multipoint analyses).

C. Linkage Disequilibrium:

To identify subregions of q11.2–q32.1 that are smaller than those identified in meiotic mapping techniques, stretches of the genetic fine structure map that may show evidence of linkage disequilibrium (i.e., association between alleles from two different genetic marker loci) are identified. (It is worthy of note that the magnitude of the linkage disequilibrium is not a reliable estimate of the location of a gene (79) and is therefore not of immediate concern in the present analyses.) The presence of a region showing linkage disequilibrium provides a possible valuable clue to further refine the map location of a chromosome 14-AD gene locus. In the case of genetic markers with only 2-alleles, measures of linkage disequilibrium may be based on samples of haplotypes (when available) or genotypes (e.g., see 80–82). The latter statistical analyses are based on non-random selection of disease genotypes and haplotypes, i.e., as necessary for analysis of genetic markers linked to a chromosome 14-AD gene locus. Individuals used in such analyses are selected from Caucasian families with a high probability for having a chromosome 14 AD trait and include only unrelated individuals: i.e., one affected individual from each family, any unaffected spouses (as controls), and relevant genetically unrelated controls. In addition to the nine ENVG families presented in Table 3 (Example 1, above), other affected and "at-risk" individuals (i.e., having a chromosome 14-AD trait) from other ENVG families, as well as, individuals from families previously designated FAD 1, FAD2, and FAD4 (4) may be useful in the analyses of linkage disequilibrium.

D. Genetic Fine Structure Mapping of a Chromosome 14-AD Gene Locus:

Chromosome 14 genetic markers such as those presented in Table 2 (above), as well as novel polymorphic markers identified in "A–C" (above), are placed on a fine structure map of subregions of q11.2–q32.1 region in relation to one another and the short tandem repeat polymorphic markers (STRP) shown in FIG. 1 and Table 1, by using standard mapping methods with a CEPH mapping panel (i.e., perfect 3 generation genomic DNA samples) and the computer program CRI-MAP.

1. Identification of New STRP Loci:

The most useful new STRP markers are commonly identified by investigators because they are highly polymorphic, abundant in the genome, can be rapidly genotyped, and are evenly distributed throughout the genome. Dinucleotide repeat (e.g., $(CA)_n$) loci are more densely distributed in the genome than tri- and tetranucleotide repeat markers, although other repeat motifs are also useful in fine structure mapping (66). $(CA)_n$ repeat markers may conveniently be isolated from a DNA library by any of a number of different methods depending upon the nature of the library. Two chromosome 14 flow-sort libraries are commercially available from the American Type Culture Collection (Rockville, Md.) that have average insert sizes of 4 kb. The clones in these libraries may be useful in constructing other libraries containing clones that have subregions of the 4 kb inserts enriched in STRP sequences, i.e., by preparing DNA fragments enriched in STRP sequences using a method similar to that described by Ostrander et al. (63). Briefly, the 4 kb inserts from the flow-sort libraries are digested with multiple restriction enzymes that cleavage a polynucleotide sequence with 4-base specificity. The resulting fragments are cloned into a phagemid vector and the resultant library of clones is amplified as single-stranded DNA using an M13 helper phage vector for infection of a dut (dUTPase) ung (uracil-N-glycosylase) strain of *E. coli* (Under these conditions single-stranded DNA with a high level of uracil (instead of thymidine) is produced.) The resulting circular single-stranded DNA of the M13 phage vector is then converted to circular double-stranded DNA, i.e., using either a $(CA)_n$ or $(GT)_n$ oligonucleotide PCR primer and Taq DNA polymerase. When the PCR product is transformed into a wild-type *E. coli* single-stranded DNA containing uracil is eliminated and the resultant DNA contains small inserts that are enriched in CA tracks (i.e., by approximately 40–50%) that can easily be sequenced. Nucleotide sequencing is conveniently performed using an ABI fluorescence-based automated sequencer. Routinely, 400–500 bp of nucleotide sequence is identified in each run using either single-stranded DNA sequencing or high-temperature double-stranded DNA cycle-sequencing. PCR primers are commonly prepared for clones that are identified with dinucleotide repeat tracts longer than 15 repeats (83). The PCR primers are next used to test panels of genomic DNA from 10 unrelated subjects to determine whether the novel STRP marker is polymorphic. Markers that are polymorphic are next tested with DNA from a chromosome 14 rodent/human somatic cell hybrids to determine the location of the novel STRP locus in relation to other known markers within the particular subregion of the q11.2q32.1 region of chromosome 14.

2. q11.2–q32.1 Subregion Specific Clones Containing STRP Genetic Markers:

Flow-sort chromosome 14 DNA libraries may also conveniently be used as a source of STRP markers for the entire q11.2–q32.1 region of chromosome 14, (e.g., using an approach such as that described in "D.1", above.) Other approaches for generating clones from subregions of the q11.2–q32.1 region of chromosome 14-AD include: a) chromosome microdissection followed by cloning the genomic DNA; and, b) constructing libraries of radiation-reduced somatic cell hybrid cell lines containing subregions of the q11.2–q32.1 region. Yeast artificial chromosome vectors containing sequence-tagged sites may also be useful in screening assays to identify additional novel STRP markers. Each of the preceding approaches is discussed in separate sections (below).

3. Genotyping STRP Markers:

All genotyping steps are conveniently performed using a 96 well microtiler plate format and the various DNA samples (i.e., from chromosome 14-AD families, CEPH families, and Caucasian and Japanese controls) may be stored in the microtiter plates until use. PCR methods are most useful for genotyping with automated micropipetting of the components of the incubation mixtures into tubes and amplification performed in a Perkin-Elmer-Cetus 9600 thermocycler. Typically one primer is end-labeled with $^{32}P$, although both strands can also be labeled during the amplification reactions (e.g., using $^{32}P$-dCTP). End-labeling is slightly more time consuming in terms of preparing the primers for PCR, however, reading genotypes from the autoradiographs is faster and more accurate using the end-labeling method. PAGE loading buffer is added directly to the PCR amplification tubes, and conventional DNA sequencing gels are loaded (72 lanes/gel; 60 genotype lanes) using a 12-place Hamilton syringe with the correct spacing for the gel lanes. Multiple loci are routinely amplified in the same PCR tube (known in the art as "multiplexing") by using several pairs of PCR primer. In some cases where multiplexing is not successful multiple loading of gel lanes with different samples, i.e., staggered loading of 2 or 3 lanes of the gel with multiple samples, is useful for increasing the number of genotypes that can be identified in a gel run, i.e., from the 60 (above) to 120–180 genotypes/gel (and occasionally to 240/gel).

Genotypes for STRP loci markers useful in constructing fine structure maps of q11.2–q32.1 subregions are conveniently determined using DNA samples collected from: ENVG families (presently approximately n=100 samples from different individuals); CEPH samples (n=510 different samples; i.e., used if a novel STRP genetic marker is not already located on the free structure map in relation to other markers); normal unrelated Caucasians (n=100), Japanese (n=100), and Mexican Hispanics (n=100). Marker allele frequencies are important in linkage analysis, particularly when numerous rare alleles exist in a population for a particular genetic marker (84). Data obtained with Japanese and Hispanic populations and families may be important in identifying such rare alleles. In certain cases where a rare allele may be segregating with a chromosome 14-AD trait, phenotype, or genetic marker, it may be necessary to collect genotype data from larger samples of a particular population. Presently, 480 unrelated Caucasian individuals (including certain CEPH individuals) and 225 Japanese samples are available for use in the assays described above.

E. Chromosome Microdissection:

Chromosome microdissection may also be used for isolating q11.2–q32.1 subregion-specific libraries that may be useful in identifying new STRP markers (above) and new anonymous sequence-tagged sites (STSs).

1. Preparation of Metaphase Chromosome Spreads:

Cells from normal fibroblast cultures are conveniently grown on glass coverslips, harvested by treating with a colcemid solution (Gibco) for 30 minutes, and lysed by hypotonic treatment in 0.75M KCI for 22–27 minutes. A brief fixation in methanol: acetic acid (9:1) is used before air drying and the coverslips may then be stored in 70% ethanol overnight. For Geimsa staining of chromosome bands (GTG banding) the coverslips are transferred into a trypsin solution (1 ml Bacto trypsin, DIFCO in 60ml Sorenson's buffer, pH 6.88) at room temperature for 30–45 seconds, rinsed briefly in 70% ethanol, and stained immediately with Wrights stain (Sigma) in hydrion buffer (Micro Essential Labs) for about 1 minute.

2. Microdissection and Microcloning:

A Zeiss Axiovert 10 microscope with rotating stage and an Eppendorf micromanipulator with homing function software is conveniently used for microdissection. A coverslip (prepared as in "E.I", above) containing metaphase chromosomal spreads and a siliconized coverslip holding a moisture chamber are assembled on a petri dish with a square cut-out. 20–40 chromosome bans are dissected from the metaphase chromosome bands using extended siliconized glass needles. The dissected band regions are transferred one at a time to the moisture chamber into 1 nl of a collection solution (10 mM Tris, pH7.5, 10 mM NaCl, 1% SDS, 1% glycerol, and 5 mg/ml proteinase K)(85). The DNA in the collection solution is digested with RsaI and the fragments so generated are ligated into an SmaI cut pUG plasmid vector. The insert DNA is conveniently amplified by PCR using DNA sequencing primers. After 26 cycles of amplification the products in the reaction mixture may be cloned into pUC13 (86,87).

3. Identification of STRP Markers in Microdissection Libraries:

Fragmented genomic DNA from subregions of q11.2–q32.1 (i.e., in pUC13, above; or other plasmid vectors), is useful in constructing DNA libraries that may be screened for STRP markers, e.g., $(CA)_n$ tracks. One simple screening procedure involves direct hybridization (e.g., in dot blots) of $^{32}$P-labeled $(CA)_{15}$ synthetic oligonucleotides to cloned DNA.

F. RH Mapping:

Radiation-hybrid (RH) maps of subregions with the q11.2–q32.1 region of chromosome 14 are constructed as described in Step 1, above. These maps have the following advantages: namely, a) markers need not be polymorphic to be placed on the map; b) high density RH maps can be constructed in a relatively short period of time; c) analysis is less time consuming than meiotic mapping; d) the potential practical limits of fine structure resolution of an RH map is greater than a genetic map; e) new markers, genes, and other loci can be placed more rapidly on an RH map; f) RH and genetic maps can be readily integrated (i.e., one into the other) by RH mapping STRP loci having a known position on a genetic map; and, g) radiation-hybrid cell lines useful for region-specific cloning are available and have been well characterized.

RH maps are useful in the following strategic experimental approaches: namely, i) STRP markers can first be placed on an RH map, and those falling adjacent to a subregion of q11.2–q32.1 can then be given top priority for genetic mapping and genotype analysis (i.e., in chromosome 14-AD kindreds); ii) The meiotic and RH maps can be used in side-by-side comparisons to resolve any ambiguous ordering of loci and to detect errors in either map, or in a clone presumed to contain a contiguous marker (or gene) sequence (i.e., also referred to below by the acronym "contig"). The RH map may also be used to verify maps assembled using pulse-field gel electrophoresis, fluorescence in situ hybridization loci ordering, and contig integrity (i.e., lack of gaps in a clone); iii) For subregions of q11.2–q32.1 lacking adequate polymorphic markers to construct a proper genetic map, YAC clones may be isolated using PCR primers constructed to identify the appropriate sequence tagged sites (STSs) in the lacking subregion of the RH maps. The resulting YAC clones can then be screened for STRP markers, and the markers identified in this manner may be used to fill in the genetic map of the lacking subregion. iv) When a chromosome 14 AD gene locus is sufficient localized within a subregion of q11.2q32.1, the subregion may be cloned (i.e., primarily using YACs vectors). The latter subregion YACs may conveniently be identified using appropriate sets of PCR primers, i.e., primers specific for the STSs mapped into the subregion. Provided that the RH map is of sufficient marker density, it may also be possible to assemble a contigous YAC clone (i.e., having the entire coding region of a chromosome 14 AD locus) with only a limited amount of chromosome walking; and, v) Radiation hybrid somatic cell lines that have isolated DNA segments from the q11.2–q32.1 region may also useful for generating other subregion-specific clones, e.g., gene sequences having repetitive Alu sequences. Using Alu-PCR techniques, a library of genomic cosmid clones may be constructed from the PCR-isolated DNA segments for the RH cell lines.

1. Radiation Hybrid Somatic Cell Clone Panel:

A large panel (i.e., 8000 clones) of radiation-reduced chromosome 14 somatic cell hybrid clonal cell lines is preferable, each cell line containing a fragment of chromosome 14.

2. Sample Size Requirements for RH Mapping:

A goal in RH mapping is to generate an RH map of sequence tagged sites in subregions of the q11.2–q32.1 region of chromosome 14 (particularly within the D14S47 to D14S48 subregion) so that markers are identified at intervals of at least 0.5–1 Mb. Sample size requirements for all of chromosome 14 have been calculated and the results indicate that approximately 200 properly spaced markers and a 100 clone panel of RH cell lines should yield a 20–30 centiray (cR) RH map of the complete chromosome. (One ray is an RH map unit corresponding to approximately 5 Mb as a series of fragments produced by an X-ray dose corresponding to about 8000 rad (88,89). It is also noteworthy that these sample size estimates are based on several assumptions about fragment sizes produced by irradiation, marker distribution, and retention probabilities of genomic DNA fragments.) Under the above X-ray dose, chromosome 14 (with a length of about 100 Mb) is expected to produce about 20 fragments. Given "M" equally-spaced markers, 20/M is the approximate probability that a chromosome break may occur between adjacent genetic markers in any single RH hybrid cell line. A chromosome break is observable only if one of the fragments created by the break is retained by the somatic hybrid cell and the other is expelled from the cell;

hence, the probability of an observable break in any one somatic cell hybrid line is about $(20/M)[2r(1-r)]=40r(1-r)/M$, where r is the probability of a fragment being retained by the somatic hybrid cell. The number of observable chromosome breaks between two adjacent genetic markers in the q11.2–q32.1 region of chromosome 14 follows a binomial distribution. Table 7 presents the expected numbers for adjacent genetic marker locus pairs in which h=0,1, 2 . . . somatic cell hybrids demonstrating the observable breaks, given a probability for retention of the chromosome fragment of 0.20.

TABLE 7

Expected Numbers of Adjacent Genetic Marker Locus Pairs (N) with Observable Chromosome Breaks in "h" Number of 100 Hybrids for 200 Genetic Markers and a Retention Probability of 0.20.

| h | 0 | 1 | 2 | 3 | 4 | 5 | >5 |
|---|---|---|---|---|---|---|---|
| N | 7.7 | 25.4 | 41.6 | 45.0 | 36.1 | 22.9 | 20.3 |

Given equal spacing of genetic markers in chromosome 14, nearly all of the markers would be expected to be separated by observable chromosome breaks, and more than 80% of the markers should be separated by at least two breaks. Of course, markers will not be equally spaced, but even so, the large majority of the 200 loci in this model will be separated by observable breaks into different clones of RH somatic hybrid cells. Also, if retention of radiation fragments by cells has a probability "r", closer to 0.50, then the numbers of obligate detectable chromosome breaks is increased and the information obtained for ordering the breaks also increases.

3. Analysis of the Radiation Hybrid Data:

The primary method of choice for analysis in RH mapping is the multipoint maximum likelihood method of Boehnke et al. (90). Following Cox et al. (89), the method assumes 1) that X-ray breakage of chromosomes occurs at random along the chromosome, and 2) that in a somatic cell hybrid, fragments are retained or lost independent of one another. Submodels can be defined by placing restrictions on the retention probabilities for chromosome fragments by cells. For example, the equal retention model assumes all fragment retention probabilities are the same, while the centromeric model assumes that fragments having the most centromeric genetic marker are retained with one probability, while all other fragments are retained with different probabilities. For models such as the latter two, calculation of the likelihood of retention scales up or down linearly with the number of markers, making it possible to calculate the likelihood for even very large numbers of genetic marker loci (90).

For calculating likelihood, an EM algorithm (91) is used to obtain the maximum likelihood for ordering of each genetic marker locus (i.e., on the RH map) as well as to estimate parameters of the model. Since empirical evidence suggests the absence of any interfering factors in X-ray breakage of chromosomes, breakage probabilities, "$\theta$", can be transformed to distance estimates "x" using the analog of Haldane's (92) no interference mapping function: namely, $x = -\ln(1-\theta)(89)$.

While calculating the maximum likelihood for a single order is relatively fast (even for M=100–200 genetic markers), identifying the order with the largest likelihood among all possibilities M!/2 orders can be approached by stepwise locus ordering (i.e., placing genetic markers stepwise on the RH map), although several other methods for combinatorial optimization of ordering also exist and may work well in resolving such potential problems, i.e., including the "branch and bound" (93) and simulated annealing methods (94). Stepwise locus ordering in RH maps is analogous to the "build option" developed by Phil Green in his program CRI-MAP (95).

Stepwise locus ordering builds locus orders one locus at a time, at each step "m" keeps track of a list of "m-locus" candidate orders. When a new locus "m+1" is added to the list, that locus is added to all the other possible positions in each of the different "m-locus" candidate ordering schemes. Among the resulting "(m+1)-locus" order schemes, only those with maximum likelihood of more than "K" times less likely than the best "(m+1)-locus" order scheme are saved. This iterative process continues until all "M" loci are added to the scheme. The larger the "K" value that is chosen, the greater the probability that all the best "M-locus" orders will be identified, (but at the possible expense of increasing the total of different number of locus ordering schemes that must be evaluated). It is efficient at each stage "m+1" to choose to add that remaining locus whose best and second best positions in the best "m-locus" scheme ordering give the largest log-likelihood difference.

In addition to maximum likelihood methods for RH mapping, the RH mapping data can be analyzed by two other methods: namely, 1) Minimization of obligate chromosome breaks (i.e., see reference 90). This non-parametric approach has the advantage of requiring fewer modeling assumptions than maximum likelihood methods (such as that discussed above), and is computationally much simpler.
2) Bayesian posterior probabilities (96) which, under the assumption of random distribution of markers, provides a direct approach (and answer) to the question of ordering RH genetic markers. Results from the three different methods can be compared and discrepancies investigated.

4. Building an RH Map:

When sufficient markers have been typed, statistical analysis can begin. First, two-locus analyses are performed (89,90) to establish the approximate distance estimates for all the different locus pairs, and to determine which sets of loci appear to be linked. In this process, locus retention probabilities may also be estimated to suggest which chromosome fragment retention models will be most appropriate. Given two or more loci with identical retention patterns in clones of RH somatic cell lines, all but one will be excluded to simplify subsequent computational analyses.

Initially, stepwise locus ordering may be useful for evaluating all linked genetic marker loci, and a relatively small "K" value (above) will be used. Theoretically, the success of such an analysis may depend upon the rate at which the number of locus ordering schemes increases during the computation of locus orders. If successful, the analyses may be repeated with a larger value of "K" to determine whether any additional ordering schemes are identified that have a maximum likelihood within say 1000:1 of the best locus ordering. If so, the process may be run again using a still larger "K" value. However, if the initial computational results fail to identify a useful ordering scheme, (i.e., because too many different locus ordering schemes develop during computation), then different subsets of the marker data may be analyzed. For example, one subset of markers may be chosen that is roughly equally spaced and appears to span the entire relevant region or subregion of q11.2–q32.1. Other subsets may then be chosen that correspond with other reasonably closely linked sets of genetic markers. Eventually, using such an approach a framework of maps of ordered genetic marker loci may be developed at 100:1 and 1000:1 relative maximum likelihoods for different regions and subregions that constitute a chromosome 14 AD gene locus region (e.g., a related approach see ref. 97). Analyses using "stepwise locus ordering" may be repeated using "simultaneous annealing," and "best identified orders," and the locus ordering scheme for each computational optimization approach compared. Analyses may also be repeated under different chromosome retention probability models. As additional markers are typed, they may be added to the RH map.

5. Influential Hybrids and Error Identification:

All genotyping for RH mapping is performed in duplicate to minimize possibilities of errors. In addition, as the construction of an RH map proceeds the possibility of data errors may be addressed as follows. First, the hybrid retention information for all loci are printed, as well as the chromosome retention values calculated for all loci, and their best locus ordering schemes. Hybrids that require a large number of obligate chromosome breaks, or that have runs of retained (or non-retained) genetic marker loci that are interrupted by a single non-retained (or retained) genetic marker locus will be considered suspect for a possible error. Second, hybrids requiring different numbers of chromosome breaks under the best several ordering schemes, or hybrids exhibiting substantially different likelihood values under the best ordering scheme, will be considered suspect. In either of the latter two cases, the suspect hybrids will be either re-scored and (if necessary) re-typed.

6. Loci for RH Mapping:

The genetic markers useful in RH mapping include genes, anonymous polymorphic loci (e.g., STRP and RFLP fragments), CpG islands, and anonymous non-polymorphic sequence-tagged sites (STSs). Sites that can be amplified by PCR are most convenient, and other types of sites will only be used if PCR methods are insufficient for the task at hand. STSs are generated by sequencing clones from a variety of sources using ABI fluorescence-based automatic sequencing.

i) Genes:

Approximately 50 genes have been assigned to chromosome 14 (Gene Data Bank/Online Medelian Inheritance in Man). STS primers may be designed using information available in published sequences for chromosome 14 genes. If no intronic sequence has been published, primers may be designed to amplify a fragment from the 3' untranslated portion of the gene's cDNA sequence. Typically the 3' untranslated sequence regions of a gene are not interrupted by introns and are not conserved across species. Thus, amplification of genomic DNA of rodent/human RH hybrid cell clones is not a problem (98).

ii) STRP and Other Polymorphic Loci:

STRP loci inherently involve PCR amplification methods (above) and are useful directly as STSs. For other polymorphic sites used in RFLP type analysis, appropriate RH clones are isolated and short stretches of nucleotide sequence determined to find sites suitable for construction of STSs. STSs based on polymorphic sites may be useful for connecting markers on the RH map with their corresponding relative location (i.e., in relation to the same polymorphic marker) on a genetic map constructed analyzing recombination of the genetic markers in chromosome 14 AD families (as described above).

iii) CpG Island Clones:

Not I and Sac II restriction fragment "linking" libraries for chromosome 14 are useful as STSs. The clones in such libraries are sequenced to determine useful STSs, and may also be useful in pulse-field gel electrophoresis mapping of chromosome 14 q11.2–q32.1 subregions.

iv) Anonymous Clones:

The clones that can be sequenced most rapidly are anonymous clones in genomic DNA and flow-sort chromosome 14 libraries. To establish a map of the entire chromosome 14 q11.2–q32.1 region, anonymous clones identified as having chromosome 14 DNA segments (above) may be sequenced. Approximately 200 STS lcoi (of all types) are needed for mapping of chromosome 14 at the level of a fine structure map with 0.5–1 Mb units.

7. Genotyping for RH Mapping:

Genotype analysis of the radiation hybrid somatic cell lines is performed using protocols similar to those described above for STRP analysis in 96 well microtiter plastes. For most loci PCR amplification products in the reaction mixtures may be visualized after agarose gel electrophoresis by staining with ethidium bromide. All genotype analyses are performed in duplicate to control for errors.

II. Step 2) YAC and Cosmid Cloning

A. YAC Cloning:

YAC clones are used for two purposes: namely, 1) analysis of STRP loci at intervals of about 1–2cM in the q11.2–q32.1 region of chromosome 14, (sequence tagged sites such as PCR primers at each end of a region of the RH map is used to identify YAC clones; in turn, the YAC clones may be screened for the presence of additional novel STRP sequences); 2) the q11.2–q32.1 region of chromosome 14 is cloned using YAC clones and a contiguous nucleotide sequence assembled from the sequence of the clones.

1. Preparation of the YAC library:

YAC libraries are prepared so that they may be screened completely by PCR-based methods without the need for oligonucleotide probe hybridization methods (99–101). YAC clones may be grown on nylon filters or in 96 well plates and pooled according to the scheme of Amemiya et al. (101). The exact numbers of pools of YAC clones is determined by the redundancy of the library selected. Likewise, the number of vertical and horizontal pools and corresponding superpools is determined by the number of clones. For example, a 55,000 clone, 5-fold coverage library is divided into 6 "sets", each set consisting of 96 vertical and 96 horizontal pools. The vertical and horizontal pools may be combined into 8 superpools each. Screening may then proceed on the superpool level (96 samples). If only one superpool is positive, the second screen is 24 samples, which theoretically yields a well containing a desired YAC clone.

2. YAC library screening:

Several methods are useful for screening YAC libraries. First, YACs may be identified by PCR amplification followed by gel electrophoresis to detect specific amplification products. Second, a combined PCR, oligonucleotide-ligation assay method (100) may be used. Such an approach has advantages of added specificity, speed (no electrophoresis is required), and automation. Third, each superpool is amplified by Alu-PCR methods and the products resolved by agarose-gel electrophoresis, transfer to nylon filters, and Southern blotting (101). The resulting filters are then be hybridized to Alu-PCR products from radiation hybrid somatic cell lines, cosmid clones, YAC dones, (or other clones) so that the candidate YAC pools are identified.

3. Characterization of YAC Clones with Subregions of q11.2–q32.1:

YAC clones of interest may also be analyzed by pulse-field gel electrophoresis and Southern blotting methods to determine the number of artificial chromosomes within a given YAC clone. Also, Alu-PCR products from YAC clones (102) or from total YAC clonal DNAs are useful for fluorescence in situ hybridization (FISH) probes for identifying chromosomal band location of the isolated DNA segment in the YAC clone. FISH is also useful for insuring that the YAC clonal DNA is from the q11.2–q32.1 region of chromosome 14 and to determine if the DNA is chimeric.

4. Identification of STRP Sites in YACs:

YAC clones are screened for the presence of STRP sites by methods described above. Since yeast have repetitive sequences (including CA tracks) initially Alu-PCR is useful to produce YAC-specific DNA. The PCR amplified DNA is conveniently analyzed by Southern blot methods using a $(CA)_n$ oligonucleotide as a probe. If a CA-repeat sequence is present, the Alu-PCR amplification products may be subcloned and sequenced. If the repeat sequence is not present, YAC DNA excised from pulse-field gel electrophoresis gels are subcloned and recombinants having the CA-repeat sequence are identified by colony hybridization methods (103).

5. Assembling a YAC Conrig:

A large number of sequence-tagged sites that are ordered on an RH map (above) may subsequently be used to identify one or more YAC clones that have a contiguous nucleotide sequence spanning subregions of q11.2–q32.1, (i.e., with a minimum of chromosome walking). The integrity of the contig YAC is established using probe-content mapping (104), and the presence (or absence) of a large number of probes may be useful in determining the presence (or absence) of overlapping regions.

B. In Situ Hybridization of Metaphase and Interphase Chromosomes:

The location of YAc and cosmid clones in the q11.2–q32.1 region of chromosome 14 may be determined by fluorescent in situ hybridization. This methodology has been used by several groups to successfully map cosmid and YAC clones (105–109). (Partial or complete physical maps of chromosomes 1, 3, 11, 16, 17, 19, and X have been developed previously using this type of approach.) The chromosome 14 map that can be constructed from FISH data may be correlated with the RH map and genetic maps, i.e., by locating the chromosomal band region location of an RH or genetic map marker. Individual genetic markers may be localized on banded prometaphase chromosomes so that an optimal resolution is provided with respect to locating the signal within a chromosomal band.

The cosmid or YAC clones from chromosome 14 may be labeled using nick-translation or random-priming with biotin or digoxygenin-substituted nucleotides. With YAC clones, Alu-PCR amplification may also be helpful for amplifying portions of the YAC clones prior to the nick translation; (see 102, 110). The latter PCR method is simpler than the isolation of YAC inserts by gel electrophoresis. The size of the PCR chemically-labeled DNA fragments may be determined using gel electrophoresis and the concentration of DNase I adjusted to obtain fragments of about 200–400 bp. The chemically-labeled DNA prepared in this manner is useful as a FISH probe for hybridization to prometaphase chromosomes in cell preparations in the presence of formamide, (i.e., using appropriate methodology to control for nonspecific hybridization with repeated DNA by prehybridizing the probes with total human DNA or Cot-1 DNA). Biotin-labeled FISH probes are conveniently visualized by reacting with fluorescein-avidin, producing a green fluorescent signal that may be amplified using a second antibody to form layers, i.e., biotinylated goat anti-avidin antibody followed by a second layer of fluorescein-avidin. The digoxygenin-labeled DNA probes may be visualized by reacting with Texas red to produce a red signal. Alternative detection systems for digoxygenin include anti-digoxygenin-fluorescein and avidin-Texas red (or rhodamine). A third type of FISH probe label may also be used, namely dinitrophenol, that can be used with cascade blue to produce light in a fluorescent wavelength distinguishable using appropriate microscopic filters. Mixtures of two or three differently labeled probes may be used in the same assay to increase the number of markers visualized (111). However, the latter approach may require computer-assisted image manipulation. At this point in the process, individual cosmid clones may be mapped with respect to one another (i.e., two at a time), thus building a physical map by pariwise comparisons of the location of fluorescent sites.

Chromosome banding is conveniently accomplished using Hoechst 33258-actinomycin D staining, or by chromomycin-distamycin staining to produce a reverse banding (R-banding) from the image obtained with the Hoechst-actinomycin D. A minimum of 20 cells is usually examined to control for variations in the technique, and assuming that the observed efficiency of hybridization is good. In some cases, more cells may need to be examined in order to visualize both signals on the same chromosome. The level of resolution commonly required for mapping DNA markers on metaphase chromosomes by in situ hybridization is in the range of 2–5 Mb. The method commonly allows assignment of cosmid or YAC clones to specific chromosomal bands, with finite relationship to the centromere of the chromosome, and with a relative relationship to each other (if the DNA markers are not too close together- in which case the signals may be superimposed).

Other methods are available to allow resolution in FISH of closely spaced markers that cannot be resolved in a condensed metaphase chromosome. Interphase mapping of nuclei may be useful where map distance are in the order of 100 kb between markers (109, 112). With interphase nuclei mapping methods, FISH probes for two (or three) different cosmid clones may be simultaneously analyzed (i.e., using different chemical labels; as above). Hypotonically lysed interphase nuclei are immobilized on slides using a chromosome fixative solution such (as that described above). Labeled FISH probes are hybridized to the DNA on the slides, and their presence is detected at the appropriate fluorescent wavelength microscopically (as above). A total of 100–200 nuclei are commonly examined for each pair of probes, and distances between the signals may be measured on images of the nuclei following the method of ven den Engh et al. (113). This approach may be used to determine the relative order of closely spaced loci that cannot be adequately resolved using RIt mapping, or standard metaphase FISH methods (above). The process may be simplified by isolating sequence-tagged sites (i.e., corresponding to the respective PCR-portions of the YAC clones or cosmid clones) from the interphase nuclear DNA prior to immobilizing the DNA for interphase FISH analysis. Such a method may also be useful for testing the integrity of any candidate "contig" clones.

III. Step 3. Identification of the Candidate Genes in the Chromosome 14 q11.2–q32.1 Subregion of Chromosome 14.

Several methods have been devised for finding genes in genomic DNA clones and in bulk sequence data (114) including: 1) the use of "zoo" blots, (i.e., using DNA from a variety of animal sources to identify evolutionarily conserved nucleotide sequences); 2) exon trapping (115); 3) nuclear HnRNA cloning from somatic cell hybrids (116); 4) homologous recombination (117); 5) hybridization of cDNAs to genomic clones on filters or in solution (118, 119); 6) hybridization of genomic clones to cDNA libraries; 7) identification of potential coding regions in genomic DNA sequence data by computer programs such as GRAIL (120); and, 8) mapping of randomly sequenced cDNA clones (ESTs; expressed sequence tags; ref. 121). For each method the YAC (or cosmid) clonal DNA (i.e., from above) may be used as starting material. Identification of candidate genes may also be achieved by sequencing the YAC (or cosmid) clonal DNA and processing the resultant nucleotide sequence data using the GRAIL computer program to identify exon sequences (i.e., candidate gene sequences). Specific hybridization of cDNA clones with YAC (or cosmid) clonal DNA immobilized on filter paper (e.g., "dot blots") may also be convenient to screen for candidate genes.

Step 4. Identification of a Chromosome 14 AD gene locus:

Small deletions (or insertions) in genetic marker alleles that are linked with a chromosome 14 Alzheimer's disease in a family, may be identified by Southern blotting methods using YAC (or cosmid) clonal DNA obtained from DNAs that are contiguous in the marker region being examined. Alleles that result from a single nucleotide base change may be identified by sequencing candidate genes, e.g., the isolated DNA segments in YAC clones. Single strand sequence analysis or DNA sequencing methods may be used to directly determine the molecular basis for the allelic variants of the genetic marker in a chromosome 14 AD family. True alleles may be distinguished from polymorphism and rare, benign sequence variants as follows: namely, 1) DNA sequence analysis is conducted of 1 AD affected, 1 unaffected, and 1 unrelated control subject from the L family (above). The latter family has the highest LOD scores for chromosome 14 AD markers and also has the highest number of affected individuals (of those families sampled). A true allele or mutation may be recognized because it will segregate with the gene in this family when all the family members are tested. 2) Families other than the L family may be tested to determine whether the same "L-family-allele" (or mutation) co-segregates with the chromosome 14 AD in the family. 3) Control populations may be tested to determine the frequency of the "L-family allele" (or mutation) in normal populations.

Citations

1. Goudsmit, J., et al., J. Neurol. Sci. 49, 79 (1981).
2. Weitkamp, L. R., et al., Am. J. Hum. Genet. 35, 443 (1983).
3. Valencia, L. G., et al., Lab. Rev. Invest. Clin. (Mex.) 38, 261 (1986).
4. St. George-Hyslop, P. H., et al., The genetic defect causing familial Alzheimer's disease maps on chromosome 21. Science 235: 885–890 1987a.
5. Bird, T. D., et al., Ann. Neurol. 23, 25 (1988).
6. Bird, T. D., et al., Phenotypic heterogeneity in familial Alzheimer's disease: A study of 24 kindreds. Ann Neurol 25: 12–25, 1989.
7. Heston, L. L., et al, Linkage of an Alzheimer disease susceptibility locus to markers on human chromosome 21. Am J Med Genet 40: 449–453, 1991.
8. Schellenberg, G. D., et al., Linkage analysis of familial Alzheimer's disease using chromosome 21 markers. Am J Hum Genet 48: 563–583, 1991.
9. Goate, A. M., et al., Segregation of a missense mutation in the amyloid precursor protein gene with familial Alzheimer's disease. Nature 349: 704–706, 1991.
10. Chartier-Harlin, M.-C., et al., Early-onset Alzheimer's disease caused by mutation at codon 717 of the $\beta$-amyloid precursor protein gene. Nature 353: 844–846, 1991.
10A. Levy, E, et al., Mutation of the Alzheimers disease amyloid gene in hereditary cerebral hemorrhage, Dutch type. Science 248: 1124–1126, 1990.
11. Murrell, J., et al., A mutation in the Amyloid Precursor protein associated with hereditary Alzheimer's disease. Science 254: 97–99, 1991.
12. Schellenberg, G. D., et al., Association of an Apolipoprotein CII allele with familial dementia of the Alzheimer type. J Neurogenet 4: 97–108, 1987.
13. Schellenberg, G. D., et al., Genetic Association and Linkage analysis of the Apo CII locus and familial Alzheimer's disease. Ann Neurol (in press).
14. Pericak-Vance, M. A., et al., Linkage studies in familial Alzheimer's disease: evidence for chromosome 19 linkage. Am J Hum Genet 48: 1034–1050, 1991.
15. Naruse, S., et al., Mis-sense mutation Val-Ile in exon 17 of amyloid precursor protein gene in Japanese familial Alzheimer's disease. Lancet 337: 978–979, 1991.
16. Yoshioka, K., et al., The $^{717}$Val-Ile substitution in amyloid precursor protein is associated with familial Alzheimer's disease regardless of ethnic groups. Biochem Biphys Res Comm 178: 1141–1146, 1991.
17. Schellenberg, G. D., et al., $APP_{717}$, $APP_{693}$, and PRIP gene mutations are rare in Alzheimer disease. Am J Hum Genet 49: 511–517, 1991.
18. Kamino, K., et al., Am. J. Hum. Genet., in press.
19. Van Duijn, C. M., et al., Amyloid precursor protein gene mutation in early-onset Alzheimer's disease. Lancet 337: 978, 1991.
20. Chartier-Harlin, M.-C., et al., Neurosci. Lett. 129, 134 (1.991).
21. Crawford, F., et al., Neurosci. Lett. 133, 1 (1991).
22. Pericak-Vance, M. A., et al., Exp. Neurol. 102, 271 (1988).
23. Van Duijn, C. M., et al., Familial aggregation of Alzheimer's disease and related disorders—A collaborative re-analysis of case-control studies. Int J Epidemiol 20: S13–S20, 1991.
24. Mohs, R. C., et al., Arch. Gen. Psychiatry 44, 405 (1987).
25. Heston, L., et al., Dementia of the Alzheimer type. Arch. Gen. Psychiatry 38: 1085–1090, 1981.
26. Rapoport, S. I., et al., Neurology 41, 1549 (1991).
27. Nee, L. E., et al., Neurology 37, 359 (1987).
28. Breitner, J. C. S., et al., Neurobiol. Aging 13, S66.
29. Bergem, A. L. M., et al., Neurobiol. Aging 13, S66.
30. Schellenberg, G. D., et al., Absence of linkage of chromosome 21 q21 markers to familial Alzheimer's disease in autopsy-documented pedigrees. Science 241: 1507–1510, 1988.
31. St George-Hyslop, P. H., et al., Genetic linkage studies suggest that Alzheimer's disease is not a single homogeneous disorder. Nature 347: 194–197, 1990.
32. Tanzi, R. E., et al., Molecular Genetics of Alzheimer disease amyloid. J Biol Chem 266: 20579–20582, 1990.
33. Schellenberg, G. D., et al., Ann. Neurol. 31, 223 (1992).
34. Tanzi, R. E., et al., The genetic defect in familial Alzheimer's disease is not tightly linked to the amyloid beta-protein gene. Nature 329: 156–157, 1987.
35. Van Broeckhoven C., et al., Failure of familial Alzheimer's disease to segregate with the A-4 amyloid gene in several European families. Nature 329: 153–155, 1987.
36. Hodge, S. E., et al., Am. J. Hum. Genet. 35, 1139 (1983).
37. Morton, N. E., Am. J. Hum. Genet. 48, 80 (1956).
38. Abraham, C. R., et al., Cell 52, 487 (1988).
39. Wang, Z., and J. L. Weber, Genomics 13, 532 (1992).
40. Ott, J., Analysis of Human Genetic Linkage (Johns Hopkins University Press, Baltimore, 1991) p 66.
41. Risch, N., Am. J. Hum. Genet. 48, 1058 (1991).
42. Williamson, R., et al., Cytogenet. Cell. Genet. 58, 1190 (1991).
43. Sheng, M., and M. E. Greenberg, Neuron 4, 477 (1990).
44. Salbaum, J. M., et al., EMBO J. 7, 2807 (1988).
45. Ruppert, C., and W. Willie, Molec. Brain Res. 2, 51 (1987).
46. Dragunow, M., and H. A. Robertson, Brain Res. 455, 295 (1988).
47. Zhang, P., et al., Neuroscience 46, 9 (1992).
48. Ellis, R. J., Annu. Rev. Biochem. 60, 321 (1991); I. R. Brown, J. Neurosci. Res. 27, 247 (1990).
49. Allen, R. E., et al., Nucl. Acids Res. 19, 1722 (1991).
50. Jordan, S. A., et al., Nucl. Acids Res. 19, 1959 (1991).
51. Long, G. L., et al., Biochemistry 23, 4828 (1983).
52. Cox, D. W., et al., Nature 316, 79 (1985).
53. Nukiwa, T., et al., J. Hum. Genet. 43,322 (1988).
54. Nukiwa, T., et al., J. Biol. Chem. 261, 15989 (1986).
55. Sharma, V., et al., Dinucleotide repeat polymorphism at the D14S43 locus. Nucl. Acids Res. 19: 1722, 1991.
56. Weber, J. L., et al., Mapping of human chromosome 5 microsatellite DNA polymorphisms. Genomics 11: 695–700, 1991.
57. Wang, Z., and J. L. Weber. Continuous linkage map of human chromosome 14 short tandem repeat polymorphisms. Genomics 13: 532–536, 1992.
58. Tsui, L-P., et al., Cystic fibrosis locus defined by a genetically linked polymorphic DNA marker. Science 230: 1054–1057, 1985.
59. Kerem, B-S., et al., Identification of the cystic fibrosis gene: genetic analysis. Science 245: 1073–1080, 1989.
60. Riordan, J. R., et al., Identification of the cystic fibrosis gene: Cloning and characterization of complementary DNA. Science 245:1066–1072, 1989.
61. Rommens, J. M., et al., Identification of the cystic fibrosis gene: Chromosome walking and jumping. Science 245: 1059–1065, 1989.
62. Hearne, C. M., et al., Microsatellites for linkage analysis of genetic traits. TIC 8:288–294, 1992.
63. Ostrander, E. A., et al., Construction of small-insert genomic DNA libraries highly enriched for microsatellite repeat sequences. Proc. Natl. Acad. Sci. (USA) 89: 3419–3423, 1992.
64. Weber, J. L., and P. E. May. Abundant class of human DNA polymorphisms which can be typed using the polymerase chain reaction. Am. J. Hum. Genet. 44: 388–396, 1989.
65. Litt, M., and J. A. Luty. A hypervariable microsatellite revealed by in vitro amplification of a dinucleotide repeat within the cardiac muscle actin gene. Am. J. Hum. Genet. 44: 397–401, 1989.
66. Edwards, A., et al., DNA typing and genetic mapping with trimeric and tetrameric tandem repeats. Am. J. Hum. Genet. 49: 746–756, 1992.
67. Korn, B., et al., A strategy for the selection of transcribed sequences in the Xq28 region. Human Molec. Genet. 1: 235–242, 1992.
68. Landegren, U., et al., A ligase-mediated gene detection technique. Science 241: 1077–1080, 1988.
69. Corbo, L, et al., Direct cloning of human transcripts with HnRNA from hybrid cell lines. Science 249: 652–655, 1990.
70. Parimoo, S., et al., cDNA selection: Efficient PCR approach for the selection of cDNAs encoded in large chromosomal DNA fragments. Proc. Natl. Acad. Sci. USA 88: 9623–9627, 1991.
71. Wyman, A. R., and R. White. A highly polymorphic locus in human DNA. Proc. Natl. Acad. Sci. 77: 6754–6758, 1990.
72. Roberts, L., GRAIL seeks out genes buried in DNA sequences. Science Nov. 8, 1991. p. 805.
73. Polymeropoulos, M. H., et al., Chromosomal assignment of 46 brain cDNAs. Genomics 12: 492–496, 1992.
74. Vogel, F., and A. G. Motulsky, Human Genetics, Second Edition, Springer-Verlag, New York, 1986.
75. Green, E D, Olsen, M V (1990) Systematic screening of yeast artificial-chromosome libraries by the use of the polymerase chain reaction. Proc. Natl. Acad. Sci. USA 87, 1213–1217.
76. Kwok, P. U., Gremaud, M F, Nickerson, D A, Hood, L, Olsen, M V (1992). Automatable screening of yeast artificial-chromosome libraries based on the oligonucleotide-ligation assays. Genomics 13, 935–941
77. Amemiya C T, Alegria-Hartman M J, Alslanidis C, Chen C, NikolicJ, Gingrich J C, de Jong P J (1992) A two-dimensional YAC pooling strategy for library screening via STS and Alu-PCR methods. Nucl. Acids Res. 20, 2559–2563
78. Silverman, G A., Jockel, J I, Domer, P H, Mohr, R M, Tailion-Miller, P, Korsmeyer, S J (1991) Yeast artificial chromosome cloning of a two megabase-size contig within chromosomal band 18q21 establishes physical linkage between BCL2 and plaminogen activator inhibitor type-2. Genomics 9, 219–228

79. Kaplan N, Weir B S (1992) Expected behavior of conditional linkage disequilibrium. Am J Hum. Genet. 51, 333–343.

80. Chakraborty, R (1986) Estimation of linkage disequilibrium from conditional haplotype data: application to beta-globin gene cluster in American blacks. Genet Epidemiol 3, 323–333.

81. Chakravarti, A, Li, C C, Buetow, Ktt (1984). Estimation of the marker gene frequency and linkagedisequilibrium from conditional marker data. Am J Hum Genet 36, 177–186.

82. Maiste, P J, Weir, B S (1992). Estimating linkage disequilibrium from conditional data. Am J Hum Genet50, 1139–1140.

84. Ott, J. (1992) Strategies for characterizing highly polymorphic markers in human gene mapping. Am. J. Hum. Genet. 51,283–290.

85. Senget, G, Ludecke, H-J, Horsthemke, B, Claussen, U (1990). Microdissection of banded human chromosomes. Hum. Genet. 84, 507–511.

86. Ludecke, H-J, Senger, G, Claussen, U, Horsthemke, B (1989). Cloning defined regions of the human-genome by microdissection of banded chromosomes and enzymatic amplification. Nature 338, 348–350.

87. Ludecke, H-J, Senger, G, Claussen, U, Horsthemke, B (1990). Construction and characterization of bandspecific DNA libraries. Hum Genet 84, 512–516.

88. Gorski, J L, Boehnke, M, Reyner, E L, Burright, E N (1992) A radiation hybrid map of the proximal shortarm of the human X chromosome spanning Incontinentia Pigmenti 1 (IP 1) translocation breakpoints. Genomics (in press).

89. Cox, D R, Burmeister, M, Price, E R, Kim, S, Myers, R M (1990). Radiation hybrid mapping: a somatic cell genetic method for constructing high-resolution maps of mammalian chromosomes. Science 250,245–250.

90. Dempster, A P, Laird, N M, Rubin, D B (1977) Maximum likelihood from incomplete data via the EM algorithm. J Roy Statist Soc B 39, 1–22.

92. Haldane, J B S (1919). The combination of linkage values, and the calculation of distance between theloci of linked factors. J. Genet. 8, 299–309

93. Nijenhuis, A, Wilf, H S (1978). Combinatorial Algorithms, 2nd ed. Academic Press, New York, pp.240–246.

94. Kirkpatrick, S, Gelatt, C D, Vecchi, M P (1983). Optimization by simulated annealing. Science 220,671–680.

95. Barker, D, Green, P, Knowlton, R G, Schumm, J W, Oliphant, A, Lander, E S et al. (1987) Genetic linkage map of human chromosome 7 with 63 DNA markers. Proc. Natl. Acad. Sci. USA 84, 8006–8010.

96. Lange K, Boehnke M (1992) Bayesian methods and optimal experimental design for gene mapping by radiation hybrids. Ann. Hum. Genet. 56: 119–144.

97. Frazer, K A, Boehnke, M, Budaft, M L, Wolff, R K, Emanuel, B S, Myers, R M, Cox, D R (1992) A radiation hybrid map of the region on human chromosome 22 containing the Neurofibromatosis type 2 locus. Genomics, (in press).

98. Wilcox, A S, Khan, A S, Hopkins, J A, Sikela, J M (1991). Use of 3′ untranslated sequences of human cDNAs for rapid chromosome assignment and conversion to STSs: implications for an expression map of the genome. Nucl. Acids. Res. 19, 1837–1843.

99. Green, E D, Olsen, M V (1990). Systematic screening of yeast artificial-chromosome libraries by the use of the polymerase chain reaction. Proc. Natl. Acad. Sci. USA 87, 1213–1217.

100. Kwok, P-U, Gremaud, M F, Nickerson, D A, Hood, L, Olsen, M V (1992). Automatable screening of yeastartificial-chromosome libraries based on the oligonucleotide-ligation assays. Genomics 13, 935–941.

101. Amemiya, C T, Alegria-Hartman, M J, Alslanidis, C, Chen, C, Nikolic, J, Gingrich, J C, de Jong, P J (1992). A two-dimensional YAC pooling strategy for library screening via STS and Alu-PCR methods. NuclAcids Res 20, 2559–2563.

102. Breen, M, Arveiler, B, Murray, I, Gosden, J R, Porteous, D J (1992). YAC mapping by FISH using Alu-PCR-generated probes. Genomics 13, 726–730.

103. Cornelis, F, Hashimoto, L, Loveridge, J, MacCarthy, A, Buckle, V, Julier, C, Bell, J (1992) Identification of a CA repeat at the TCRA locus using yeast artificial chromosomes: a general method for generating highly polymorphic markers at chosen loci. Gertomits 13, 820–825.

104. Zuo, J, Robbins, C, Tailion-Miller, P, Cox, D R, Myers, R M (1992). Cloning of the Huntington disease region in yeast artificial chromosomes. Hum Molec Genet 1, 149–160.

105. Lichter, P, Tang, C, Call, K, Hermanson, G, Evans, C A, Housman, D, Ward, D C (1990) High-resolutionmapping of human chromosome 11 by in situ hybridization with cosmid genes. Science 247, 64–69.

106. Montanaro, V, Casamassimi, A, D'Urso, M, Yoon, J-Y, Freije, W, Schlessinger, D, Muenke, M,Nussbaum, R L, Saccone, S, Maugeri, S, Santoro, A M, Motta, S, Della Valle, G (1991). In situ hybridization to cytogenetic bands of yeast artificial chromosomes covering 50% of human Xq24–Xq28 DNA. Am. J. Hum. Genet. 48, 183–194.

107. Driesen, M S, Dauwerse, J G, Wapenaar, M C, Meershoek, E J, Mollevanger, P, Chen, K L, Fischbeck, K H, van Ommen, G J B. (1991). Generation and fluorescent in situ hybridization mapping of yeast artificialchromosomes of 1p, 17p, 17q, and 19q from a hybrid cell line by high-density screening of an amplified library. Genomics 11, 1079–1087.

108. Takahashi, E-I, Yamakawa, K, Nakamura, Y, Hori, T-A (1992). A high-resolution cytogenetic map of human chromosome 3: Localization of 291 new cosmid markers by direct R-banding fluorescence in sire hybridization. Genomics 13, 1047–1055.

109. Trask, B J, Pinkel, D, van den Engh, G J. (1989). The proximity of DNA sequences in interphase cell nuclei is correlated to genomic distance and permits ordering of cosmids spanning 250 kilobase pairs. Genomics 5, 710–717.

110. Baldini, A, Ross, M, Nizetic, D, Vatcheva, R, Lindsay, E A, Lehrach, H, Siniscalco, M (1992) Chromosomal assignment of human YAC clones by fluorescence in situ hybridization: Use of single-yeast-colony PCR and multiple labeling. Genomics 14, 181–184.

111. Ried, T, Baldini, A, Rand, T C, Ward, D C (1992). Simultaneous visualization of seven different DNA probes by in situ hybridization using combinatorial fluorescence and digital imaging microscopy. Proc. Natl. Acad. Sci. USA 89, 1388–1392.
112. Lawrence, J B, Villnave, C A, Singer, R H (1988). Sensitive, high-resolution chromatin and chromosome mapping in situ: Presence and orientation of two closely integrated copies of EBV in a lymphoma-line. Cell 52, 51–61.
113. Van den Engh, G, Sachs, R, Trask, B J (1992). Estimating genomic distance from DNA sequencelocation in cell nuclei by a random walk model. Science 257, 1410–1412.
114. Hochgeschwender, U (1992). Toward a transcriptional map of the human genome. TIG 8, 41–43.
115. Duyk, G M, Kim, S, Myers, R M, and Cox, D R (1990). Exon trapping: a genetic screen to identify candidate transcribed sequences in cloned mammalian genomic DNA. Proc Natl Acad Sci USA 87,8995–8999.
116. Corbo, L, Maley, J A, Nelson, D L, Caskey, C T (1990). Direct cloning of human transcripts with HnRNA from hybrid cell lines. Science 249, 652–655.
1.17. Kurnit, D M, Seed, B (1990). Improved genetic selection for screening bacteriophage libraries by homologous recombination in vivo. Proc Natl Acad Sci USA 87, 3166–3169.
118. Parimoo, S, Patanjali, S R, Shukla, H, Chaplin, D, Weissman, S M (1991). cDNA selection: Efficient PCR approach for the selection of cDNAs encoded in large chromosomal DNA fragments. Proc. Natl. Acad. Sci. USA 88, 9623–9627.
119. Korn, B, Sedlacek, Z, Manca, A, Kioschis, P, Konecki, D, Lehrach, H, Poustka, A (1992). A strategy for the selection of transcribed sequences in the Xq28 region. Hum Molec Genet 4, 235–242.
120. Uberbacher, E C, Mural, R J (1991). Locating protein-coding regions in human DNA sequences by a multiple sensor-neural network approach. Proc Natl Acad Sci USA 88, 11261–11265.
121. Polymeropoulos, M H, Xiao, H, Glodek, A, Gorski, M, Adams, M D, Moreno, R F, Fitzgerald, M G, Venter, J C, Merril, C R (1992). Chromosomal assignment of 46 brain cDNAs. Genomics 12, 492–496.

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. A method for isolating a DNA segment indicative of an early-onset familial Alzheimer's disease trait in a family population, wherein said family population consists essentially of a plurality of blood relatives of an individual having a chromosome 14 early-onset familial Alzheimer's disease trait, comprising the steps of:
   preparing a test sample of immobilized separated genomic DNA fragments from a plurality of the blood relatives,
   contacting each of the test samples with a test oligonucleotide under conditions permitting hybridization of complementary single stranded DNA molecules, wherein the test oligonucleotide specifically hybridizes to a nucleotide sequence between markers D14S52 and D14S53,
   identifying a plurality of hybridized molecules so formed as alleles of the genetic marker in the family population,
   identifying one of the genetic marker alleles as indicative of the Alzheimer's disease trait in the family population by either
   determining by pedigree analysis a segregation value for each of the genetic marker alleles and the Alzheimer's disease trait, and selecting an indicative genetic marker allele that co-segregates with the Alzheimer's disease trait in the family population, or
   measuring genetic linkage between each of the genetic marker alleles and the Alzheimer's disease trait, and selecting a genetic marker allele as indicative of the Alzheimer's disease trait in the family population if the selected genetic marker allele has a maximal LOD score of at least 3 at a recombination fraction of about 0.0 to about 0.1 for genetic linkage with the Alzheimer's disease trait in the family population, and
   isolating a DNA segment comprising the indicative genetic marker allele.

2. The method of claim 1, wherein the immobilized separated genomic DNA fragments are selected from the group consisting of restriction fragment length polymorphism fragments, short and long tandem repeat fragments, PCR fragments, and fragments having a repetitive nucleotide sequence.

3. A PCR assay for testing an individual for genetic predisposition for a chromosome 14 early-onset familial Alzheimer's disease trait, comprising the steps:
   preparing a test sample of immobilized isolated single stranded PCR regions of genomic DNA from a first individual by
   contacting a genomic DNA sample from the first individual with at least two oligonucleotide PCR primers under conditions suitable for hybridization, wherein the PCR primers are capable of hybridizing under stringent conditions with a genetic marker genetically linked and co-segregating with a chromosome 14 early-onset familial Alzheimer's disease trait in a family population, wherein the family population consists essentially of a plurality of blood relatives of both the first individual and a second individual having the chromosome 14 early-onset familial Alzheimer's disease trait, and wherein said genetic marker consists of a nucleotide sequence that specifically hybridizes to a nucleotide sequence between markers D14S52 and D14S53 and is characterized by having a maximal LOD score of at least 3 at a recombination fraction of about 0.0 to about 0.1 for genetic linkage with the chromosome 14 early-onset familial Alzheimer's disease trait in the family population, and
   amplifying and immobilizing PCR regions hybridizing with the PCR primers, and
   determining that the first individual is genetically predisposed to a chromosome 14 early-onset familial Alzheimer's disease if the amplified PCR regions comprise the genetic marker.

4. An assay for detecting in a DNA sample a genetic marker that is genetically linked and co-segregating with an early-onset familial Alzheimer's disease trait in a family population, wherein the family population consists essentially of a plurality of blood relatives of an individual having the early-onset familial Alzheimer's disease trait, wherein the genetic marker consists of a nucleotide sequence that specifically hybridizes to a nucleotide sequence between markers D14S52 and D14S53 and is characterized by having a maximal LOD score of at least 3 at a recombination fraction of about 0.0 to about 0.1 for genetic linkage with the early-onset familial Alzheimer's disease trait in the family, said assay comprising the steps of:
   collecting a test sample of genomic DNA from an individual, and separating and immobilizing a plurality of single stranded fragments of said genomic DNA on a solid phase,
   contacting said immobilized fragments with a test oligonucleotide probe under conditions permitting hybridization of complementary single stranded DNA molecules, wherein said test oligonucleotide probe is complementary with at least a portion of said nucleotide sequence, and
   identifying hybridized molecules so formed to detect whether the sample of genomic DNA of the individual comprises the genetic marker.

5. The assay of claim 4, wherein the plurality of single stranded fragments of said genomic DNA are selected from the group consisting of restriction fragment length polymorphism fragments, short and long tandem repeat fragments, PCR fragments, and fragments having repetitive nucleotide sequences.

* * * * *

UNITED STATES PATENT AND TRADEMARK OFFICE
CERTIFICATE OF CORRECTION

PATENT NO. : 5,449,604
DATED : September 12, 1995
INVENTOR(S) : G.D. Schellenberg et al.

Page 1 of 2

It is certified that error appears in the above-indentified patent and that said Letters Patent is hereby corrected as shown below:

| COLUMN | LINE | |
|---|---|---|
| 3 | 38 | "q11.214 q32.1" should read --q11.2-q32.1-- |
| 4 | 59 | "allels" should read --alleles-- |
| 5 | 27 | "Alzheimer's" should read --Alzheimer's-- |
| 8 | 60 | "flow-son" should read --flow-sort-- |
| 20 | 62 | "conrig" should read --contig-- |
| 23 | 33 | "2" should read --2†-- |
| 23 | 34 | "1" should read --1†-- |
| 23 | 42 | "Includes" should read --†Includes-- |
| 24 | 47 | "chromosome21," should read --chromosome 21,-- |
| 31 | 1 | "14" should read --19-- |
| 31 | 8 | "P 17595r" should read --P17595r-- |
| 34 | 66 | "FAD 1," should read --FAD1,-- |
| 43 | 8 | "dones," should read --clones-- |

UNITED STATES PATENT AND TRADEMARK OFFICE
CERTIFICATE OF CORRECTION

PATENT NO. : 5,449,604
DATED : September 12, 1995
INVENTOR(S) : G.D. Schellenberg et al.

It is certified that error appears in the above-indentified patent and that said Letters Patent is hereby corrected as shown below:

| COLUMN | LINE | |
|---|---|---|
| 45 | 5 | "RIt" should read --RH-- |
| 48 | 14 | "TIC" should read --TIG-- |
| 48 | 67 | "Tailion-" should read --Taillon--- |
| 49 | 20 | "51,283-290." should read --51, 283-290.-- |
| 49 | 60 | "Budaft," should read --Budarf,-- |
| 50 | 26 | "Tailion-" should read --Taillon--- |
| 51 | 22 | "1.17." should read --117.-- |

Signed and Sealed this

Fourteenth Day of May, 1996

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES:24

( 2 ) INFORMATION FOR SEQ ID NO:1:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION: D14S47 genetic marker; Table 1

( i x ) SEQUENCE DESCRIPTION: SEQ ID NO:1:

CAACATAGCA AGACCCTGTC                     20

( 2 ) INFORMATION FOR SEQ ID NO:2:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION: D14S47 genetic marker; Table 1

( i x ) SEQUENCE DESCRIPTION: SEQ ID NO:2:

GCACATGCCA CCAAGACAAG                     20

( 2 ) INFORMATION FOR SEQ ID NO:3:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:D14S52 genetic marker; Table 1

( i x ) SEQUENCE DESCRIPTION: SEQ ID NO:3:

TTACTCCCTG CAAAACAAAC                     20

( 2 ) INFORMATION FOR SEQ ID NO:4:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:D14S52 genetic marker; Table 1

( i x ) SEQUENCE DESCRIPTION: SEQ ID NO:4:

GATGAATTTC AGAAATGGAG        20

( 2 ) INFORMATION FOR SEQ ID NO:5:

( i ) SEQUENCE CHARACTERISTICS:
        ( A ) LENGTH:19 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:D14S53 genetic marker; Table 1

( i x ) SEQUENCE DESCRIPTION: SEQ ID NO:5:

CAACAAGAGC GAAACTCGC        19

( 2 ) INFORMATION FOR SEQ ID NO:6:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:D14S53 genetic marker; Table 1

( i x ) SEQUENCE DESCRIPTION: SEQ ID NO:6:

GAAGACTCAA GATATAGCAG        20

( 2 ) INFORMATION FOR SEQ ID NO:7:

( i ) SEQUENCE CHARACTERISTICS:
        ( A ) LENGTH:19 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:D14S55 genetic marker; Table 1

( i x ) SEQUENCE DESCRIPTION: SEQ ID NO:7:

AGAACTGTTA CCTGGAGGC        19

( 2 ) INFORMATION FOR SEQ ID NO:8:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:D14S55 genetic marker; Table 1

( i x ) SEQUENCE DESCRIPTION: SEQ ID NO:8:

AGAGAAGTTA AAAGCATTGC        20

( 2 ) INFORMATION FOR SEQ ID NO:9:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i i ) MOLECULE TYPE:oligonucleotide
        ( A ) DESCRIPTION:D14S48 genetic marker; Table 1

( i x ) SEQUENCE DESCRIPTION: SEQ ID NO:9:

CATAAAAGGC TTATTGGTTT G                                                                                                      2 1

( 2 ) INFORMATION FOR SEQ ID NO:10:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i i ) MOLECULE TYPE:oligonucleotide
        ( A ) DESCRIPTION:D14S48 genetic marker; Table 1

( i x ) SEQUENCE DESCRIPTION: SEQ ID NO:10:

CAAAACAGAG AACAGAGTAG                                                                                                        2 0

( 2 ) INFORMATION FOR SEQ ID NO:11:

( i ) SEQUENCE CHARACTERISTICS:
        ( A ) LENGTH:16 base pairs
        ( B ) TYPE:nucleic acid
        ( C ) STRANDEDNESS:single
        ( D ) TOPOLOGY:linear ( i i i ) MOLECULE TYPE:oligonucleotide
        ( A ) DESCRIPTION:D14S43 genetic marker; Table 1

( i x ) SEQUENCE DESCRIPTION: SEQ ID NO:11:

TGGAACACTC AGGCGA                                                                                                              1 6

( 2 ) INFORMATION FOR SEQ ID NO:12:

( i ) SEQUENCE CHARACTERISTICS:
        ( A ) LENGTH:17 base pairs
        ( B ) TYPE:nucleic acid
        ( C ) STRANDEDNESS:single
        ( D ) TOPOLOGY:linear ( i i i ) MOLECULE TYPE:oligonucleotide
        ( A ) DESCRIPTION:D14S43 genetic marker; Table 1

( i x ) SEQUENCE DESCRIPTION: SEQ ID NO:12:

CCAGAGCCAC TTTCTAC                                                                                                        1 7

( 2 ) INFORMATION FOR SEQ ID NO:13:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i i ) MOLECULE TYPE:oligonucleotide
        ( A ) DESCRIPTION:brain chromosome 14 primer EST00221

( i x ) SEQUENCE DESCRIPTION: SEQ ID NO:13:

GTGCCAAGAT GGCTCATGTA                                                                                      2 0

( 2 ) INFORMATION FOR SEQ ID NO:14:

( i ) SEQUENCE CHARACTERISTICS:
    ( A ) LENGTH:20 base pairs
    ( B ) TYPE:nucleic acid
    ( C ) STRANDEDNESS:single
    ( D ) TOPOLOGY:linear ( i i ) MOLECULE TYPE:oligonucleotide
    ( A ) DESCRIPTION:brain chromosome 14 primer EST00221

( i x ) SEQUENCE DESCRIPTION: SEQ ID NO:14:

GTATAGCTTT AAGCCAGTTC                                                    20

( 2 ) INFORMATION FOR SEQ ID NO:15:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:brain chromosome 14 primer EST00201

( i x ) SEQUENCE DESCRIPTION: SEQ ID NO:15:

CCAGGAGAGT AAGAAGATCA                                                    20

( 2 ) INFORMATION FOR SEQ ID NO:16:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:brain chromosome 14 primer EST00201

( i x ) SEQUENCE DESCRIPTION: SEQ ID NO:16:

GCAGAGTTGA ATATGAACCT                                                    20

( 2 ) INFORMATION FOR SEQ ID NO:17:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:brain chromosome 14 primer EST00008

( i x ) SEQUENCE DESCRIPTION: SEQ ID NO:17:

AAGCTGGCTG GGAAATGTTC                                                    20

( 2 ) INFORMATION FOR SEQ ID NO:18:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:brain chromosome 14 primer ( i x ) SEQUENCE DESCRIPTION: SEQ ID NO:18:

GTCAGTCTAG TAAACTTACA C                                                  21

( 2 ) INFORMATION FOR SEQ ID NO:19:

( i ) SEQUENCE CHARACTERISTICS:
        ( A ) LENGTH:21 base pairs ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:PI40471 gene sequence primer; Example 1

( i x ) SEQUENCE DESCRIPTION: SEQ ID NO:19:

AGTGAAGTCA TTTACCCCAG G 21

( 2 ) INFORMATION FOR SEQ ID NO:20:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:PI4047R gene sequence primer; Example 1

( i x ) SEQUENCE DESCRIPTION: SEQ ID NO:20:

GGTTCATTAT GCCTCCCAAG C 21

( 2 ) INFORMATION FOR SEQ ID NO:21:

( i ) SEQUENCE CHARACTERISTICS:
        ( A ) LENGTH:22 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:PI gene sequence primer;PI75951; Example 1

( i x ) SEQUENCE DESCRIPTION: SEQ ID NO:21:

GCTGACACTC ACGATGAAAT CC 22

( 2 ) INFORMATION FOR SEQ ID NO:22:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:PI gene sequence primer;PI7595r; Example 1

( i x ) SEQUENCE DESCRIPTION: SEQ ID NO:22:

ACTTATCCAC TAGCTTCAGG C 21

( 2 ) INFORMATION FOR SEQ ID NO:23:

( i ) SEQUENCE CHARACTERISTICS:
        ( A ) LENGTH:21 base pairs
        ( B ) TYPE:nucleic acid
        ( C ) STRANDEDNESS:single
        ( D ) TOPOLOGY:linear ( i i ) MOLECULE TYPE:oligonucleotide
        ( A ) DESCRIPTION:PI gene sequence primer;PI93501; Example 1

( i x ) SEQUENCE DESCRIPTION: SEQ ID NO:23:

TCTGCTACAC TCTTCCAAAC C 21

( 2 ) INFORMATION FOR SEQ ID NO:24:

( i ) SEQUENCE CHARACTERISTICS:
        ( A ) LENGTH:22 base pairs
        ( B ) TYPE:nucleic acid
        ( C ) STRANDEDNESS:single (D) TOPOLOGY:linear (ii) MOLECULE TYPE:oligonucleotide
    (A) DESCRIPTION:PI gene sequence primer;PI9350r; Example 1

(ix) SEQUENCE DESCRIPTION: SEQ ID NO:24:

GGTGAGTTCA TTTACCAGGT GC　　　　　　　　　　　　　　　　22